(12) United States Patent
Shenoy et al.

(10) Patent No.: US 11,517,360 B2
(45) Date of Patent: Dec. 6, 2022

(54) METHOD AND APPARATUS FOR TREATING CANINE CRUCIATE LIGAMENT DISEASE

(71) Applicant: The Foundry, LLC, Menlo Park, CA (US)

(72) Inventors: Vivek Shenoy, Redwood City, CA (US); Mark Deem, Mountain View, CA (US)

(73) Assignee: The Foundry, LLC, Menlo Park, CA (US)

( * ) Notice: Subject to any disclaimer, the term of this patent is extended or adjusted under 35 U.S.C. 154(b) by 724 days.

(21) Appl. No.: 15/864,796

(22) Filed: Jan. 8, 2018

(65) Prior Publication Data

US 2018/0125550 A1 May 10, 2018

Related U.S. Application Data

(63) Continuation of application No. 14/642,121, filed on Mar. 9, 2015, now Pat. No. 9,861,408, which is a continuation of application No. PCT/US2013/058877, filed on Sep. 10, 2013, said application No. 14/642,121 is a continuation-in-part of application No. 13/002,829, filed as application No. PCT/US2010/046996 on Aug. 27, 2010, now Pat. No. 9,795,410.

(Continued)

(51) Int. Cl.
*A61F 2/08* (2006.01)
*A61B 17/56* (2006.01)
*A61B 17/80* (2006.01)

(52) U.S. Cl.
CPC .......... *A61B 17/8061* (2013.01); *A61B 17/56* (2013.01)

(58) Field of Classification Search
CPC .......... A61F 2/3886; A61F 2002/30703; A61F 2/38; A61F 2/3877; A61F 2/389; A61B 17/56; A61B 2017/564; A61B 2017/565; A61B 17/8872; A61B 17/8061
See application file for complete search history.

(56) References Cited

U.S. PATENT DOCUMENTS 2,632,440 A 3/1953 Hauser
2,877,033 A 3/1959 Koetke
(Continued)

FOREIGN PATENT DOCUMENTS

CA 1205602 6/1986
CN 2788765 6/2006
(Continued)

OTHER PUBLICATIONS

Lapinskaya, Valentina Spiridonovna, "Treatment of Diseases and Injuries of Hip Joint Using a Method of Distraction", Kuibyshev Medical Institute, 1990.

(Continued)

*Primary Examiner* — Ann Schillinger
(74) *Attorney, Agent, or Firm* — Downs Rachlin Martin PLLC

(57) ABSTRACT

Prostheses and methods for treating canine cruciate ligament disease are disclosed comprising placement of a specifically configured implant on the femur or tibia to displace targeted muscle or connective tissue associated with the stifle joint so as to reduce cranial tibial thrust.

13 Claims, 13 Drawing Sheets

Related U.S. Application Data

(60) Provisional application No. 61/699,089, filed on Sep. 10, 2012, provisional application No. 61/237,518, filed on Aug. 27, 2009, provisional application No. 61/288,692, filed on Dec. 21, 2009.

(56) References Cited

U.S. PATENT DOCUMENTS

| | | |
|---|---|---|
| 3,242,922 A | 3/1966 | Thomas |
| 3,648,294 A | 3/1972 | Shahrestani |
| 3,681,786 A | 8/1972 | Lynch |
| 3,779,654 A | 12/1973 | Horne |
| 3,872,519 A | 3/1975 | Giannestras et al. |
| 3,875,594 A | 4/1975 | Lynch |
| 3,879,767 A | 4/1975 | Stubstad |
| 3,886,599 A | 6/1975 | Schlien |
| 3,889,300 A | 6/1975 | Smith |
| 3,902,482 A | 9/1975 | Taylor |
| 3,985,127 A | 10/1976 | Volkov et al. |
| 3,988,783 A | 11/1976 | Treace |
| 4,007,495 A | 2/1977 | Frazier |
| 4,041,550 A | 8/1977 | Frazier |
| 4,052,753 A | 10/1977 | Dedo |
| 4,054,955 A | 10/1977 | Seppo |
| 4,069,518 A | 1/1978 | Groth, Jr. et al. |
| 4,156,944 A | 6/1979 | Schreiber et al. |
| 4,158,894 A | 6/1979 | Worrell |
| 4,164,793 A | 8/1979 | Swanson |
| 4,187,841 A | 2/1980 | Knutson |
| 4,246,660 A | 1/1981 | Wevers |
| 4,285,070 A | 8/1981 | Averill |
| 4,308,863 A | 1/1982 | Fischer |
| 4,353,361 A | 10/1982 | Foster |
| 4,367,562 A | 1/1983 | Gauthier |
| 4,470,158 A | 9/1984 | Pappas et al. |
| 4,501,266 A | 2/1985 | McDaniel |
| 4,570,625 A | 2/1986 | Harris |
| 4,576,158 A | 3/1986 | Boland |
| 4,621,627 A | 11/1986 | DeBastiani et al. |
| 4,637,382 A | 1/1987 | Walker |
| 4,642,122 A | 2/1987 | Steffee |
| 4,696,293 A | 9/1987 | Ciullo |
| 4,759,765 A | 7/1988 | Van Kampen |
| 4,759,766 A | 7/1988 | Buettner-Janz et al. |
| 4,776,851 A | 10/1988 | Bruchman et al. |
| 4,778,472 A | 10/1988 | Homsy et al. |
| 4,846,842 A | 7/1989 | Connolly et al. |
| 4,863,471 A | 9/1989 | Mansat |
| 4,871,367 A | 10/1989 | Christensen et al. |
| 4,873,967 A | 10/1989 | Sutherland |
| 4,883,486 A | 11/1989 | Kapadia et al. |
| 4,904,261 A | 2/1990 | Dove et al. |
| 4,919,672 A | 4/1990 | Millar et al. |
| 4,923,471 A | 5/1990 | Morgan |
| 4,942,875 A | 7/1990 | Hlavacek et al. |
| 4,955,915 A | 9/1990 | Swanson |
| 4,959,065 A | 9/1990 | Arnett et al. |
| 4,988,349 A | 1/1991 | Pennig |
| 4,988,350 A | 1/1991 | Herzberg |
| 5,002,574 A | 3/1991 | May et al. |
| 5,011,497 A | 4/1991 | Persson et al. |
| 5,019,077 A | 5/1991 | DeBastiani et al. |
| 5,019,104 A | 5/1991 | Whiteside et al. |
| 5,026,372 A | 6/1991 | Sturtzkopf et al. |
| 5,035,700 A | 7/1991 | Kenna |
| 5,041,112 A | 8/1991 | Mingozzi et al. |
| 5,100,403 A | 3/1992 | Hotchkiss et al. |
| 5,103,811 A | 4/1992 | Crupi |
| 5,121,742 A | 6/1992 | Engen |
| 5,152,280 A | 10/1992 | Danieli |
| 5,152,790 A | 10/1992 | Rosenberg et al. |
| 5,197,966 A | 3/1993 | Sommerkamp |
| 5,197,986 A | 3/1993 | Mikhail |
| 5,231,977 A | 8/1993 | Graston |
| 5,258,032 A | 11/1993 | Bertin |
| 5,304,180 A | 4/1994 | Slocum |
| 5,314,481 A | 5/1994 | Bianco |
| 5,318,567 A | 6/1994 | Vichard |
| 5,326,364 A | 6/1994 | Clift, Jr. et al. |
| 5,352,190 A | 10/1994 | Fischer |
| 5,375,823 A | 12/1994 | Navas |
| 5,383,937 A | 1/1995 | Mikhail |
| 5,405,347 A | 4/1995 | Lee et al. |
| 5,415,661 A | 5/1995 | Holmes |
| 5,425,775 A | 6/1995 | Kovacevic et al. |
| 5,456,722 A | 10/1995 | McLeod et al. |
| 5,480,443 A | 1/1996 | Elias |
| 5,540,688 A | 7/1996 | Navas |
| 5,545,229 A | 8/1996 | Parsons et al. |
| 5,571,198 A | 11/1996 | Drucker et al. |
| 5,575,819 A | 11/1996 | Amis |
| 5,578,038 A | 11/1996 | Slocum |
| 5,580,353 A | 12/1996 | Mendes et al. |
| 5,601,553 A | 2/1997 | Trebling et al. |
| 5,624,440 A | 4/1997 | Huebner |
| 5,662,648 A | 9/1997 | Faccioli et al. |
| 5,662,650 A | 9/1997 | Bailey et al. |
| 5,676,667 A | 10/1997 | Hausman |
| 5,681,313 A | 10/1997 | Diez |
| 5,695,496 A | 12/1997 | Orsak et al. |
| 5,702,460 A | 12/1997 | Carls et al. |
| 5,702,465 A | 12/1997 | Burkinshaw |
| 5,702,467 A | 12/1997 | Gabriel et al. |
| 5,716,357 A | 2/1998 | Rogozinski |
| 5,733,287 A | 3/1998 | Tepic et al. |
| 5,749,872 A | 5/1998 | Kyle et al. |
| 5,766,251 A | 6/1998 | Koshino |
| 5,803,924 A | 9/1998 | Oni et al. |
| 5,824,106 A | 10/1998 | Fournol |
| 5,871,540 A | 2/1999 | Weissman et al. |
| 5,873,843 A | 2/1999 | Draper |
| 5,879,386 A | 3/1999 | Jore |
| 5,888,203 A | 3/1999 | Goldberg |
| 5,928,234 A | 7/1999 | Manspeizer |
| 5,944,757 A | 8/1999 | Grammont |
| 5,976,125 A | 11/1999 | Graham |
| 5,976,136 A | 11/1999 | Bailey et al. |
| 5,989,292 A | 11/1999 | van Loon |
| 6,036,691 A | 3/2000 | Richardson |
| 6,096,040 A | 8/2000 | Esser |
| 6,113,637 A | 9/2000 | Gill et al. |
| 6,132,468 A | 10/2000 | Mansmann |
| 6,139,550 A | 10/2000 | Michelson |
| 6,143,032 A | 11/2000 | Schafer et al. |
| 6,146,423 A | 11/2000 | Cohen et al. |
| 6,161,080 A | 12/2000 | Aouni-Ateshian et al. |
| 6,162,223 A | 12/2000 | Orsak et al. |
| 6,176,860 B1 | 1/2001 | Howard |
| 6,193,225 B1 | 2/2001 | Watanabe |
| 6,200,347 B1 | 3/2001 | Anderson et al. |
| D443,060 S | 5/2001 | Benirschke et al. |
| 6,245,110 B1 | 6/2001 | Grundei et al. |
| 6,264,696 B1 | 7/2001 | Reigner et al. |
| 6,277,124 B1 | 8/2001 | Haag |
| 6,280,474 B1 | 8/2001 | Cassidy et al. |
| 6,302,915 B1 | 10/2001 | Cooney, III et al. |
| 6,315,798 B1 | 11/2001 | Ashby et al. |
| 6,315,852 B1 | 11/2001 | Magrini et al. |
| 6,355,037 B1 | 3/2002 | Crosslin et al. |
| 6,364,881 B1 | 4/2002 | Apgar et al. |
| 6,368,326 B1 | 4/2002 | Dakin et al. |
| 6,371,985 B1 | 4/2002 | Goldberg |
| 6,409,729 B1 | 6/2002 | Martinelli et al. |
| 6,409,767 B1 | 6/2002 | Perice et al. |
| 6,468,314 B2 | 10/2002 | Schwartz et al. |
| 6,482,232 B1 | 11/2002 | Boucher et al. |
| 6,485,503 B2 | 11/2002 | Jacobs et al. |
| 6,494,914 B2 | 12/2002 | Brown et al. |
| 6,520,964 B2 | 2/2003 | Tallarida et al. |
| 6,527,733 B1 | 3/2003 | Ceriani et al. |
| 6,540,708 B1 | 4/2003 | Manspeizer |
| 6,572,653 B1 | 6/2003 | Simonson |
| 6,579,318 B2 | 6/2003 | Varga et al. |
| 6,589,248 B1 | 7/2003 | Hughes |

(56) References Cited

U.S. PATENT DOCUMENTS

| | | | |
|---|---|---|---|
| 6,592,622 | B1 | 7/2003 | Ferguson |
| 6,599,321 | B2 | 7/2003 | Hyde, Jr. |
| 6,599,322 | B1 | 7/2003 | Amrich et al. |
| 6,616,696 | B1 | 9/2003 | Merchant |
| 6,620,332 | B2 | 9/2003 | Amrich |
| 6,623,486 | B1 | 9/2003 | Weaver et al. |
| 6,626,945 | B2 | 9/2003 | Simon et al. |
| 6,632,247 | B2 | 10/2003 | Boyer, II et al. |
| 6,652,529 | B2 | 11/2003 | Swanson |
| 6,663,631 | B2 | 12/2003 | Kuntz |
| 6,679,914 | B1 | 1/2004 | Gabbay |
| 6,692,497 | B1 | 2/2004 | Tormala et al. |
| 6,692,498 | B1 | 2/2004 | Niiranen et al. |
| 6,702,821 | B2 | 3/2004 | Bonutti |
| 6,709,460 | B2 | 3/2004 | Merchant |
| 6,712,856 | B1 | 3/2004 | Carignan et al. |
| 6,719,794 | B2 | 4/2004 | Gerber |
| 6,752,831 | B2 | 6/2004 | Sybert et al. |
| 6,770,078 | B2 | 8/2004 | Bonutti |
| 6,800,094 | B2 | 10/2004 | Burkinshaw |
| 6,814,757 | B2 | 11/2004 | Kopylov et al. |
| 6,824,567 | B2 | 11/2004 | Tornier et al. |
| 6,852,125 | B2 | 2/2005 | Simon et al. |
| 6,852,330 | B2 | 2/2005 | Bowman et al. |
| 6,854,330 | B2 | 2/2005 | Potter |
| 6,855,150 | B1 | 2/2005 | Linehan |
| 6,866,684 | B2 | 3/2005 | Fell et al. |
| 6,884,242 | B2 | 4/2005 | LeHuec et al. |
| 6,890,358 | B2 | 5/2005 | Ball et al. |
| 6,893,463 | B2 | 5/2005 | Fell et al. |
| 6,896,702 | B2 | 5/2005 | Collazo |
| 6,905,513 | B1 | 6/2005 | Metzger |
| 6,911,044 | B2 | 6/2005 | Fell et al. |
| 6,916,341 | B2 | 7/2005 | Rolston |
| 6,926,739 | B1 | 8/2005 | O'Connor et al. |
| 6,966,910 | B2 | 11/2005 | Ritland |
| 6,966,928 | B2 | 11/2005 | Fell et al. |
| 6,972,020 | B1 | 12/2005 | Grayson et al. |
| 6,974,480 | B2 | 12/2005 | Messerli et al. |
| 6,994,730 | B2 | 2/2006 | Posner |
| 6,997,940 | B2 | 2/2006 | Bonutti |
| 7,004,971 | B2 | 2/2006 | Serhan et al. |
| 7,008,452 | B2 | 3/2006 | Hawkins |
| 7,011,687 | B2 | 3/2006 | Deffenbaugh et al. |
| 7,018,418 | B2 | 3/2006 | Amrich et al. |
| 7,025,790 | B2 | 4/2006 | Parks et al. |
| 7,029,475 | B2 | 4/2006 | Pajabi |
| 7,060,073 | B2 | 6/2006 | Frey et al. |
| 7,105,025 | B2 | 9/2006 | Castro et al. |
| 7,105,027 | B2 | 9/2006 | Lipman et al. |
| 7,124,762 | B2 | 10/2006 | Carter et al. |
| 7,128,744 | B2 | 10/2006 | Weaver et al. |
| 7,141,073 | B2 | 11/2006 | May et al. |
| 7,160,333 | B2 | 1/2007 | Plouhar et al. |
| 7,163,563 | B2 | 1/2007 | Schwartz et al. |
| 7,182,787 | B2 | 2/2007 | Hassler et al. |
| 7,188,626 | B2 | 3/2007 | Foley et al. |
| 7,201,728 | B2 | 4/2007 | Sterling |
| 7,223,292 | B2 | 5/2007 | Messerli et al. |
| 7,226,482 | B2 | 6/2007 | Messerli et al. |
| 7,226,483 | B2 | 6/2007 | Gerber et al. |
| 7,235,077 | B1 | 6/2007 | Wang et al. |
| 7,235,102 | B2 | 6/2007 | Ferree et al. |
| 7,238,203 | B2 | 7/2007 | Bagga et al. |
| 7,241,298 | B2 | 7/2007 | Nemec et al. |
| 7,247,157 | B2 | 7/2007 | Prager et al. |
| 7,252,670 | B2 | 8/2007 | Morrison et al. |
| 7,261,739 | B2 | 8/2007 | Ralph et al. |
| 7,273,481 | B2 | 9/2007 | Lombardo et al. |
| 7,276,070 | B2 | 10/2007 | Muckter |
| 7,282,065 | B2 | 10/2007 | Kirschman |
| 7,285,134 | B2 | 10/2007 | Berry et al. |
| 7,288,094 | B2 | 10/2007 | Lindemann et al. |
| 7,288,095 | B2 | 10/2007 | Baynham et al. |
| 7,291,150 | B2 | 11/2007 | Graf |
| 7,291,169 | B2 | 11/2007 | Hodorek |
| 7,297,161 | B2 | 11/2007 | Fell |
| 7,306,605 | B2 | 12/2007 | Ross |
| 7,322,983 | B2 | 1/2008 | Harris |
| 7,322,984 | B2 | 1/2008 | Doubler et al. |
| 7,323,012 | B1 | 1/2008 | Stone et al. |
| 7,341,589 | B2 | 3/2008 | Weaver et al. |
| 7,341,590 | B2 | 3/2008 | Ferree |
| 7,341,602 | B2 | 3/2008 | Fell et al. |
| 7,361,196 | B2 | 4/2008 | Fallin et al. |
| 7,476,225 | B2 | 1/2009 | Cole |
| 7,479,160 | B2 | 1/2009 | Branch et al. |
| 7,485,147 | B2 | 2/2009 | Pappas et al. |
| 7,500,991 | B2 | 3/2009 | Bartish, Jr. et al. |
| 7,534,270 | B2 | 5/2009 | Ball |
| 7,544,210 | B2 | 6/2009 | Schaefer et al. |
| 7,553,331 | B2 | 6/2009 | Manspeizer |
| 7,572,291 | B2 | 8/2009 | Gil et al. |
| 7,611,540 | B2 | 11/2009 | Clifford et al. |
| 7,618,454 | B2 | 11/2009 | Bentley et al. |
| 7,632,310 | B2 | 12/2009 | Clifford et al. |
| 7,632,311 | B2 | 12/2009 | Seedhom et al. |
| 7,637,953 | B2 | 12/2009 | Branch et al. |
| 7,641,689 | B2 | 1/2010 | Fell et al. |
| 7,655,029 | B2 | 2/2010 | Niederberger et al. |
| 7,655,041 | B2 | 2/2010 | Clifford et al. |
| 7,678,147 | B2 | 3/2010 | Clifford et al. |
| 7,722,676 | B2 | 5/2010 | Hanson et al. |
| 7,723,395 | B2 | 5/2010 | Ringeisen et al. |
| 7,726,319 | B1 | 6/2010 | Boyce |
| 7,744,638 | B2 | 6/2010 | Orbay |
| 7,749,276 | B2 | 7/2010 | Fitz |
| 7,758,651 | B2 | 7/2010 | Chauhan et al. |
| 7,780,670 | B2 | 8/2010 | Bonutti |
| 7,806,898 | B2 | 10/2010 | Justin et al. |
| 7,819,918 | B2 | 10/2010 | Malaviya et al. |
| 7,828,852 | B2 | 11/2010 | Bonutti |
| 7,846,211 | B2 | 12/2010 | Clifford et al. |
| 7,875,082 | B2 | 1/2011 | Naidu |
| 7,879,105 | B2 | 2/2011 | Schmieding et al. |
| 7,896,921 | B2 | 3/2011 | Smith et al. |
| 7,896,923 | B2 | 3/2011 | Blackwell et al. |
| 7,951,176 | B2 | 5/2011 | Grady et al. |
| 7,959,675 | B2 | 6/2011 | Gately |
| 7,967,863 | B2 | 6/2011 | Frey et al. |
| 7,972,383 | B2 | 7/2011 | Goldstein et al. |
| 3,002,833 | A1 | 8/2011 | Monterumici et al. |
| 3,002,837 | A1 | 8/2011 | Stream et al. |
| 7,993,402 | B2 | 8/2011 | Sidler |
| 8,002,841 | B2 | 8/2011 | Hasselman |
| 3,034,117 | A1 | 10/2011 | Matsuzaki et al. |
| 3,043,380 | A1 | 10/2011 | Park et al. |
| 8,043,375 | B2 | 10/2011 | Strzepa et al. |
| 8,052,753 | B2 | 11/2011 | Melvin |
| 8,052,755 | B2 | 11/2011 | Naidu |
| 8,083,746 | B2 | 12/2011 | Novak |
| 8,088,166 | B2 | 1/2012 | Makower et al. |
| 8,088,168 | B2 | 1/2012 | Hassler et al. |
| 8,092,530 | B2 | 1/2012 | Strzepa et al. |
| 8,092,544 | B2 | 1/2012 | Wright et al. |
| 8,100,967 | B2 | 1/2012 | Makower et al. |
| 8,114,156 | B2 | 2/2012 | Hatch |
| 8,123,805 | B2 | 2/2012 | Makower et al. |
| 8,128,697 | B2 | 3/2012 | Fell et al. |
| 8,128,704 | B2 | 3/2012 | Brown et al. |
| 8,142,503 | B2 | 3/2012 | Malone |
| 8,257,444 | B2 | 9/2012 | Linares |
| 8,262,707 | B2 | 9/2012 | Huebner et al. |
| 8,267,972 | B1 | 9/2012 | Gehlert |
| 8,282,681 | B2 | 10/2012 | McLeod |
| 8,292,955 | B2 | 10/2012 | Robinson |
| 8,328,805 | B2 | 12/2012 | Cole |
| 8,372,078 | B2 | 2/2013 | Collazo |
| 8,382,807 | B2 | 2/2013 | Austin et al. |
| 8,523,921 | B2 | 9/2013 | Horan et al. |
| 8,523,948 | B2 | 9/2013 | Slone et al. |
| 8,597,362 | B2 | 12/2013 | Shenoy et al. |
| 8,771,363 | B2 | 7/2014 | Grotz |
| 8,845,724 | B2 | 9/2014 | Shenoy et al. |

(56) References Cited

U.S. PATENT DOCUMENTS

| | | |
|---|---|---|
| 8,964,106 B2 | 2/2015 | Miyata |
| 8,986,311 B2 | 3/2015 | Boudreault |
| 9,114,016 B2 | 8/2015 | Shenoy |
| 9,216,091 B2 | 12/2015 | Hardy |
| 9,278,004 B2 * | 3/2016 | Shenoy .................. A61B 17/56 |
| 9,668,868 B2 * | 6/2017 | Shenoy .............. A61B 17/1675 |
| 9,795,410 B2 * | 10/2017 | Shenoy .................. A61B 17/56 |
| 9,861,408 B2 | 1/2018 | Shenoy |
| 9,931,136 B2 | 4/2018 | Shenoy |
| 10,299,939 B2 | 5/2019 | Gonzalez-Hernandez |
| 10,349,980 B2 | 7/2019 | Shenoy |
| 2001/0020143 A1 | 9/2001 | Stark et al. |
| 2001/0023371 A1 | 9/2001 | Bonutti |
| 2001/0037155 A1 | 11/2001 | Merchant |
| 2002/0013587 A1 | 1/2002 | Winquist et al. |
| 2002/0029045 A1 | 3/2002 | Bonutti |
| 2002/0029084 A1 | 3/2002 | Paul et al. |
| 2002/0052606 A1 | 5/2002 | Bonutti |
| 2002/0065560 A1 | 5/2002 | Varga et al. |
| 2002/0091447 A1 | 7/2002 | Shimp et al. |
| 2002/0095154 A1 | 7/2002 | Atkinson et al. |
| 2002/0107574 A1 | 8/2002 | Boehm et al. |
| 2002/0133230 A1 | 9/2002 | Repicci |
| 2002/0151978 A1 | 10/2002 | Zacouto et al. |
| 2002/0165550 A1 | 11/2002 | Frey et al. |
| 2003/0055500 A1 | 3/2003 | Fell et al. |
| 2003/0083751 A1 | 5/2003 | Tornier |
| 2003/0088315 A1 | 5/2003 | Supinski |
| 2003/0100950 A1 | 5/2003 | Moret |
| 2003/0109928 A1 | 6/2003 | Pasquet et al. |
| 2003/0120344 A1 | 6/2003 | Michelson |
| 2003/0120346 A1 | 6/2003 | Mercinek et al. |
| 2003/0125807 A1 | 7/2003 | Lambrecht et al. |
| 2003/0139813 A1 | 7/2003 | Messerli et al. |
| 2003/0204265 A1 | 10/2003 | Short et al. |
| 2003/0216809 A1 | 11/2003 | Ferguson |
| 2004/0054409 A1 | 3/2004 | Harris |
| 2004/0117020 A1 | 6/2004 | Frey et al. |
| 2004/0127990 A1 | 7/2004 | Bartish, Jr. et al. |
| 2004/0133278 A1 | 7/2004 | Marino et al. |
| 2004/0143336 A1 | 7/2004 | Burkinshaw |
| 2004/0143338 A1 | 7/2004 | Burkinshaw |
| 2004/0148026 A1 | 7/2004 | Bonutti |
| 2004/0167630 A1 | 8/2004 | Rolston |
| 2004/0172133 A1 | 9/2004 | Gerber et al. |
| 2004/0186585 A1 | 9/2004 | Feiwell |
| 2004/0215195 A1 | 10/2004 | Shipp et al. |
| 2004/0230303 A1 | 11/2004 | Gomes et al. |
| 2004/0230315 A1 | 11/2004 | Ek |
| 2004/0236428 A1 | 11/2004 | Burkinshaw et al. |
| 2004/0243240 A1 | 12/2004 | Beaurain et al. |
| 2004/0260302 A1 | 12/2004 | Manspeizer |
| 2004/0267179 A1 | 12/2004 | Leman |
| 2004/0267375 A1 | 12/2004 | Friedrichs |
| 2005/0004671 A1 | 1/2005 | Ross et al. |
| 2005/0027360 A1 | 2/2005 | Webb et al. |
| 2005/0033424 A1 | 2/2005 | Fell |
| 2005/0033426 A1 | 2/2005 | Ogilvie et al. |
| 2005/0043808 A1 | 2/2005 | Felt et al. |
| 2005/0049708 A1 | 3/2005 | Atkinson et al. |
| 2005/0049711 A1 | 3/2005 | Ball |
| 2005/0085815 A1 | 4/2005 | Harms et al. |
| 2005/0119664 A1 | 6/2005 | Carignan et al. |
| 2005/0119744 A1 | 6/2005 | Buskirk et al. |
| 2005/0137708 A1 | 6/2005 | Clark |
| 2005/0143822 A1 | 6/2005 | Paul |
| 2005/0143830 A1 | 6/2005 | Marcinek et al. |
| 2005/0154390 A1 | 7/2005 | Biedermann et al. |
| 2005/0192674 A1 | 9/2005 | Ferree |
| 2005/0222685 A1 | 10/2005 | Hayden et al. |
| 2005/0251080 A1 | 11/2005 | Hyde |
| 2005/0261680 A1 | 11/2005 | Draper |
| 2005/0261767 A1 | 11/2005 | Anderson et al. |
| 2005/0267584 A1 | 12/2005 | Burdulis et al. |
| 2005/0273114 A1 | 12/2005 | Novak |
| 2005/0288788 A1 | 12/2005 | Dougherty-Shah |
| 2006/0036321 A1 | 2/2006 | Henninger et al. |
| 2006/0064169 A1 | 3/2006 | Ferree |
| 2006/0074492 A1 | 4/2006 | Frey |
| 2006/0085069 A1 | 4/2006 | Kim |
| 2006/0100715 A1 | 5/2006 | De Villiers |
| 2006/0106460 A1 | 5/2006 | Messerli et al. |
| 2006/0122620 A1 | 6/2006 | Kim |
| 2006/0129243 A1 | 6/2006 | Wong et al. |
| 2006/0142858 A1 | 6/2006 | Colleran et al. |
| 2006/0149274 A1 | 7/2006 | Justin et al. |
| 2006/0161260 A1 | 7/2006 | Thomas et al. |
| 2006/0074423 A1 | 8/2006 | Alleyne |
| 2006/0178744 A1 | 8/2006 | de Villiers et al. |
| 2006/0235387 A1 | 10/2006 | Peterman |
| 2006/0276907 A1 | 12/2006 | Boyer, II et al. |
| 2007/0027547 A1 | 2/2007 | Rydell et al. |
| 2007/0043356 A1 | 2/2007 | Timm et al. |
| 2007/0106299 A1 | 5/2007 | Manspeizer |
| 2007/0129804 A1 | 6/2007 | Bentley et al. |
| 2007/0129809 A1 | 6/2007 | Meridew et al. |
| 2007/0173946 A1 | 6/2007 | Bonutti |
| 2007/0161993 A1 | 7/2007 | Lowery et al. |
| 2007/0168033 A1 | 7/2007 | Kim et al. |
| 2007/0168036 A1 | 7/2007 | Ainsworth et al. |
| 2007/0198088 A1 | 8/2007 | Biedermann et al. |
| 2007/0198091 A1 | 8/2007 | Boyer et al. |
| 2007/0203581 A1 | 8/2007 | Vanaclocha |
| 2007/0208343 A1 | 9/2007 | Magerl et al. |
| 2007/0225820 A1 | 9/2007 | Thomas et al. |
| 2007/0233141 A1 | 10/2007 | Park et al. |
| 2007/0244483 A9 | 10/2007 | Winslow et al. |
| 2007/0244488 A1 | 10/2007 | Metzger et al. |
| 2007/0265708 A1 | 11/2007 | Brown et al. |
| 2007/0276491 A1 | 11/2007 | Ahrens |
| 2007/0288014 A1 | 12/2007 | Shadduck et al. |
| 2007/0293947 A1 | 12/2007 | Mansmann |
| 2007/0299528 A9 | 12/2007 | Lotke |
| 2008/0015591 A1 | 1/2008 | Castaneda et al. |
| 2008/0015592 A1 | 1/2008 | Long et al. |
| 2008/0015593 A1 | 1/2008 | Pfefferie et al. |
| 2008/0015603 A1 | 1/2008 | Collazo |
| 2008/0015604 A1 | 1/2008 | Collazo |
| 2008/0021566 A1 | 1/2008 | Peters et al. |
| 2008/0033552 A1 | 2/2008 | Lee et al. |
| 2008/0044449 A1 | 2/2008 | McKay |
| 2008/0071373 A1 | 3/2008 | Molz et al. |
| 2008/0071375 A1 | 3/2008 | Carver et al. |
| 2008/0091270 A1 | 4/2008 | Millet et al. |
| 2008/0097434 A1 | 4/2008 | Moumene et al. |
| 2008/0097441 A1 | 4/2008 | Hayes et al. |
| 2008/0097617 A1 | 4/2008 | Fellinger et al. |
| 2008/0132954 A1 | 6/2008 | Sekhon et al. |
| 2008/0140094 A1 | 6/2008 | Schwartz et al. |
| 2008/0140213 A1 | 6/2008 | Ammann et al. |
| 2008/0154311 A1 | 6/2008 | Staeubli |
| 2008/0154371 A1 | 6/2008 | Fell et al. |
| 2008/0154378 A1 | 6/2008 | Pelo |
| 2008/0161815 A1 | 7/2008 | Schoenefeld et al. |
| 2008/0161933 A1 | 7/2008 | Grotz et al. |
| 2008/0195099 A1 | 8/2008 | Minas |
| 2008/0200995 A1 | 8/2008 | Sidebotham |
| 2008/0208341 A1 | 8/2008 | McCormack |
| 2008/0208346 A1 | 8/2008 | Schwartz |
| 2008/0234686 A1 | 9/2008 | Beaurain et al. |
| 2008/0262549 A1 | 10/2008 | Bennett et al. |
| 2008/0262618 A1 | 10/2008 | Hermsen et al. |
| 2008/0275509 A1 | 11/2008 | Clifford et al. |
| 2008/0275552 A1 | 11/2008 | Makower et al. |
| 2008/0275555 A1 | 11/2008 | Makower et al. |
| 2008/0275556 A1 | 11/2008 | Makower et al. |
| 2008/0275557 A1 | 11/2008 | Makower et al. |
| 2008/0275558 A1 | 11/2008 | Clifford et al. |
| 2008/0275559 A1 | 11/2008 | Makower et al. |
| 2008/0275560 A1 | 11/2008 | Clifford et al. |
| 2008/0275561 A1 | 11/2008 | Clifford et al. |
| 2008/0275562 A1 * | 11/2008 | Clifford ................ A61B 17/68 623/20.21 |
| 2008/0275563 A1 | 11/2008 | Makower et al. |

(56) References Cited

U.S. PATENT DOCUMENTS

| | | |
|---|---|---|
| 2008/0275564 A1 | 11/2008 | Makower et al. |
| 2008/0275565 A1 | 11/2008 | Makower et al. |
| 2008/0275567 A1 | 11/2008 | Makower et al. |
| 2008/0275571 A1 | 11/2008 | Clifford et al. |
| 2008/0281422 A1 | 11/2008 | Schmieding |
| 2008/0281425 A1 | 11/2008 | Thalgott et al. |
| 2009/0012615 A1 | 1/2009 | Fell |
| 2009/0014016 A1 | 1/2009 | Clifford et al. |
| 2009/0018656 A1 | 1/2009 | Clifford et al. |
| 2009/0018665 A1 | 1/2009 | Clifford et al. |
| 2009/0036893 A1 | 2/2009 | Kartalian et al. |
| 2009/0048683 A1 | 2/2009 | Morris et al. |
| 2009/0076605 A1 | 3/2009 | Linares |
| 2009/0082808 A1 | 3/2009 | Butler |
| 2009/0088763 A1 | 4/2009 | Aram et al. |
| 2009/0088846 A1 | 4/2009 | Myung et al. |
| 2009/0112268 A1 | 4/2009 | Cole |
| 2009/0118830 A1 | 5/2009 | Fell |
| 2009/0132047 A1 | 5/2009 | Mansmann |
| 2009/0164014 A1 | 6/2009 | Liljensten et al. |
| 2009/0182433 A1 | 7/2009 | Reiley et al. |
| 2009/0187252 A1 | 7/2009 | Howald |
| 2009/0198341 A1 | 8/2009 | Choi et al. |
| 2009/0210063 A1 | 8/2009 | Barrett |
| 2009/0226068 A1 | 9/2009 | Fitz et al. |
| 2009/0248026 A1 | 10/2009 | Draper |
| 2009/0259311 A1 | 10/2009 | Shterling et al. |
| 2009/0259312 A1 | 10/2009 | Shterling et al. |
| 2009/0275945 A1 | 11/2009 | Makower |
| 2009/0306783 A1 | 12/2009 | Blum |
| 2009/0312807 A1 | 12/2009 | Boudreault et al. |
| 2009/0318924 A1 | 12/2009 | Helenbolt et al. |
| 2009/0318976 A1 | 12/2009 | Gabriel et al. |
| 2010/0023126 A1 | 1/2010 | Grotz |
| 2010/0023127 A1 | 1/2010 | Shohat |
| 2010/0049322 A1 | 2/2010 | McKay |
| 2010/0049325 A1 | 2/2010 | Biedermann et al. |
| 2010/0057216 A1 | 3/2010 | Gannoe et al. |
| 2010/0076564 A1 | 3/2010 | Schilling et al. |
| 2010/0106247 A1 | 4/2010 | Makower et al. |
| 2010/0106248 A1 | 4/2010 | Makower et al. |
| 2010/0114322 A1 | 5/2010 | Clifford et al. |
| 2010/0121355 A1 | 5/2010 | Sittings et al. |
| 2010/0121457 A1 | 5/2010 | Clifford et al. |
| 2010/0125266 A1 | 5/2010 | Deem et al. |
| 2010/0131068 A1 | 5/2010 | Brown et al. |
| 2010/0131069 A1* | 5/2010 | Halbrecht .............. A61F 2/3877 623/20.2 |
| 2010/0137996 A1 | 6/2010 | Clifford et al. |
| 2010/0145449 A1 | 6/2010 | Makower et al. |
| 2010/0161057 A1 | 6/2010 | Berry et al. |
| 2010/0168857 A1 | 7/2010 | Hatch |
| 2010/0198354 A1 | 8/2010 | Halbrecht |
| 2010/0204798 A1 | 8/2010 | Gerbec et al. |
| 2010/0262246 A1 | 10/2010 | Attia |
| 2010/0292731 A1 | 11/2010 | Gittings et al. |
| 2010/0292733 A1 | 11/2010 | Hendricksen et al. |
| 2010/0305698 A1 | 12/2010 | Metzger et al. |
| 2010/0305708 A1 | 12/2010 | Lang et al. |
| 2011/0004305 A1 | 1/2011 | Jansson et al. |
| 2011/0054627 A1 | 3/2011 | Bear |
| 2011/0060422 A1 | 3/2011 | Makower et al. |
| 2011/0093073 A1 | 4/2011 | Gatt et al. |
| 2011/0093079 A1 | 4/2011 | Slone et al. |
| 2011/0093080 A1 | 4/2011 | Slone et al. |
| 2011/0121457 A1 | 5/2011 | Clevenger et al. |
| 2011/0137415 A1 | 6/2011 | Clifford et al. |
| 2011/0172768 A1 | 7/2011 | Cragg et al. |
| 2011/0178603 A1 | 7/2011 | Long |
| 2011/0202138 A1 | 8/2011 | Shenoy et al. |
| 2011/0213466 A1 | 9/2011 | Shenoy et al. |
| 2011/0224734 A1 | 9/2011 | Schelling |
| 2011/0230919 A1 | 9/2011 | Alleyne |
| 2011/0230972 A1 | 9/2011 | Katrana |
| 2011/0238180 A1 | 9/2011 | Fritz et al. |
| 2011/0245928 A1 | 10/2011 | Landry et al. |
| 2011/0264216 A1 | 10/2011 | Makower et al. |
| 2011/0270393 A1 | 11/2011 | Marvel |
| 2011/0276097 A1 | 11/2011 | Raven, III |
| 2011/0288643 A1 | 11/2011 | Linder-Ganz et al. |
| 2012/0022649 A1 | 1/2012 | Robinson et al. |
| 2012/0022655 A1 | 1/2012 | Clifford |
| 2012/0046754 A1 | 2/2012 | Clifford et al. |
| 2012/0053644 A1 | 3/2012 | Landry et al. |
| 2012/0065640 A1 | 3/2012 | Metzger et al. |
| 2012/0116522 A1 | 5/2012 | Makower et al. |
| 2012/0136449 A1 | 5/2012 | Makower et al. |
| 2012/0179273 A1 | 7/2012 | Clifford et al. |
| 2012/0197410 A1 | 8/2012 | Horan et al. |
| 2012/0221106 A1 | 8/2012 | Makower et al. |
| 2012/0271366 A1 | 10/2012 | Katrana et al. |
| 2012/0290088 A1 | 11/2012 | Amirouche et al. |
| 2013/0013066 A1 | 1/2013 | Landry et al. |
| 2013/0013067 A1 | 1/2013 | Landry et al. |
| 2013/0018479 A1 | 1/2013 | Grotz |
| 2013/0041416 A1 | 2/2013 | Regala et al. |
| 2013/0096629 A1 | 4/2013 | Rollinghoff et al. |
| 2013/0150977 A1 | 6/2013 | Gabriel et al. |
| 2013/0166036 A1 | 6/2013 | De Cortanze et al. |
| 2013/0190886 A1 | 7/2013 | Tepic et al. |
| 2013/0204378 A1 | 8/2013 | Slone et al. |
| 2013/0211521 A1 | 8/2013 | Shenoy et al. |
| 2013/0289728 A1 | 10/2013 | Makower et al. |
| 2013/0304208 A1 | 11/2013 | Clifford et al. |
| 2013/0325123 A1 | 12/2013 | Clifford et al. |
| 2013/0338783 A1 | 12/2013 | Slone et al. |
| 2014/0052266 A1 | 2/2014 | Slone et al. |
| 2014/0128974 A1 | 5/2014 | Bromer |
| 2014/0156004 A1 | 6/2014 | Shenoy et al. |
| 2014/0156005 A1 | 6/2014 | Shenoy et al. |
| 2014/0257292 A1 | 9/2014 | Embleton et al. |
| 2014/0343675 A1 | 11/2014 | Valeeuwen |
| 2014/0371864 A1 | 12/2014 | Shohat |
| 2016/0213402 A1 | 7/2016 | Shenoy |
| 2016/0256286 A1 | 9/2016 | Morris |
| 2017/0027708 A1 | 2/2017 | Shenoy |
| 2018/0206887 A1* | 7/2018 | Shenoy .................. A61B 17/56 |

FOREIGN PATENT DOCUMENTS

| | | |
|---|---|---|
| DE | 19855254 A1 | 6/2000 |
| EP | 0383419 A1 | 8/1990 |
| EP | 0953317 B1 | 4/2004 |
| EP | 1410769 A2 | 4/2004 |
| EP | 1770302 A1 | 4/2007 |
| EP | 1429675 B1 | 10/2007 |
| EP | 1682020 B1 | 10/2007 |
| EP | 1847228 A1 | 10/2007 |
| EP | 1847229 A2 | 10/2007 |
| EP | 1005290 B1 | 2/2008 |
| EP | 1468655 B1 | 5/2008 |
| EP | 2452641 A1 | 5/2012 |
| FR | 2926456 A1 | 7/2009 |
| GB | 1507953 | 4/1978 |
| GB | 2223406 | 4/1990 |
| GB | 2250919 | 10/1993 |
| JP | 59131348 | 7/1984 |
| JP | 7100159 | 4/1995 |
| JP | 2532346 B2 | 11/1996 |
| JP | 2000503865 | 4/2000 |
| JP | 2001145647 | 5/2001 |
| JP | 2003102744 | 4/2003 |
| JP | 2006280951 | 10/2006 |
| JP | 2007167318 | 7/2007 |
| JP | 2007167319 | 7/2007 |
| JP | 2007170969 | 7/2007 |
| JP | 2011519303 T | 7/2011 |
| NZ | 533300 | 2/2005 |
| RU | 2085148 | 7/1997 |
| RU | 2217105 C2 | 11/2003 |
| RU | 2241400 C2 | 12/2004 |
| SU | 578063 A1 | 10/1977 |
| SU | 578957 A1 | 11/1977 |
| SU | 624613 A1 | 9/1978 |

(56) References Cited

FOREIGN PATENT DOCUMENTS

| | | |
|---|---|---|
| SU | 640740 A1 | 1/1979 |
| SU | 704605 A1 | 12/1979 |
| SU | 719612 A1 | 3/1980 |
| SU | 741872 A1 | 6/1980 |
| SU | 1186204 | 10/1985 |
| SU | 1251889 | 8/1986 |
| SU | 1316666 A1 | 6/1987 |
| SU | 1588404 | 8/1990 |
| SU | 1699441 A1 | 12/1991 |
| SU | 1769868 A1 | 10/1992 |
| WO | 1989010730 A1 | 11/1989 |
| WO | 91/07137 | 5/1991 |
| WO | 94/06364 A1 | 3/1994 |
| WO | 96/19944 A1 | 7/1996 |
| WO | 2004019831 A2 | 3/2004 |
| WO | 2004024037 A2 | 3/2004 |
| WO | 2006045091 A2 | 4/2006 |
| WO | 2006049993 | 5/2006 |
| WO | 2006110578 A3 | 10/2006 |
| WO | 2007056645 A2 | 5/2007 |
| WO | 2007090009 A1 | 8/2007 |
| WO | 2007090015 A1 | 8/2007 |
| WO | 2007090017 A1 | 8/2007 |
| WO | 2007106962 A1 | 9/2007 |
| WO | 2007109132 A2 | 9/2007 |
| WO | 2007109140 A2 | 9/2007 |
| WO | 2007109417 A2 | 9/2007 |
| WO | 2007109436 A2 | 9/2007 |
| WO | 2007114769 A1 | 10/2007 |
| WO | 2007117571 A2 | 10/2007 |
| WO | 2008006098 A2 | 1/2008 |
| WO | 2009009618 A1 | 1/2009 |
| WO | 2009018365 A1 | 2/2009 |
| WO | 2011025959 A1 | 3/2011 |
| WO | 2012062908 A1 | 5/2012 |

OTHER PUBLICATIONS

Larionov D. Yu, et al., "Medical Devices," Scientific and Technical Bimonthly Journal, May-Jun. 2008.
Lapinskaya, V.S., et al., "An Endoapparatus for Restoration of the Hip Joint," Writers Collective, 2008, UDK 615.472.03:616.728.2-089.28; pp. 8-12.
Tomita, Naohide, "Development of Treatment Devices for Cartilage Regeneration", BME vol. 16, No. 2.
Lentsner, A.A., et al., "Device For Functional Relief of Hip Joint in Cotyloid Cavity Fracture Cases", Ortop Travmatol Protez. Apr. 1990 (4) 44-6.
Aldegheri, Roberto, M.C., et al.; "Articulated Distraction of the Hip Conservative Surgery for Arthritis in Young Patients," Clinical Orthopaedics and Related Research, No. 301, pp. 94-101.
Andriacchi, Thomas P., Ph.D et al.; "Methods for Evaluating the Progression of Osteoarthritis"; Journal of Rehabilitation Research and Development, vol. 37, No. 2., Mar./Apr. 2000, pp. 163-170.
Arendt, Elizabeth, M.D.; "Anatomy and Malalignment of the Patellofemoral Joint—Its Relation to Patellofemoral Arthrosis"; Clinical Orthopaedics and Related Research; 2005, No. 436, pp. 71-75.
Benzel, Edward; "Qualitative Attributes of Spinal Implants"; in: Biomechanics of Spine Stabilization, 1995, pp. 137-150.
Buckwalter, Joseph A.; "Joint Distraction for Osteoarthritis"; The Lancet, Department of Orthopaedic Surgery, University of Iowa Hospitals and Clinics, vol. 347, Feb. 3, 1996, pp. 279-280.
Coathup, M.J. et al.; "Osseo-mechanical induction of extra-cortical plates with reference to their surface properties and gemoetric designs", Elsevier, Biomaterials 20 (1999) pp. 793-800.
Deie, Masataka, M.D. et al.; "A New Articulated Distraction Arthroplasty Device for Treatment of the Osteoarthritic Knee Joint: A Preliminary Report"; Arthroscopy: The Journal of Arthroscopic and Related Surgery; vol. 23, No. Aug. 8, 2007: pp. 833-838.
Dienst, M. et al.; "Dynamic External Fixation for Distal Radius Fractures"; Clinical Orthopaedics and Related Research, 1997, vol. 338, pp. 160-171.

Gunther, Klaus-Peter, M.D.; "Surgical Approaches for Osteoarthritis"; Best Practice & Research Clinical Rheumatology, vol. 15, No. 4, 2001, pp. 627-643.
Hall, J. et al.; "Use of a Hinged External Fixator for Elbow instability after Severe Distal Humeral Fracture"; Journal of Orthopaedic Trauma, 2000, vol. 14, No. 6, pp. 442-448.
Klein, D. et al.; "Percutaneous Treatment of Carpal, Metacarpal, and Phalangeal Injuries"; Clinical Orthopaedics and Related Research, 2000, vol. 375, pp. 116-125.
Krakauer J. et al.; "Hinged Device for Fractures involving the Proximal Interphalangeal Joint"; Clinical Orthopaedics and Related Research, 1996, vol. 327, pp. 29-37.
Leon, Heriberto Ojeda, M.D. et al.; "Minimally Invasive Selective Osteotomy of the Knee: A New Surgical Technique"; Arthroscopy: The Journal of Arthroscopic and Related Surgery, vol. 17, No. 5 (May-Jun.), 2001: pp. 510-516.
Madey, S. et al.; "Hinged External Fixation of the elbow: optimal axis alignment to minimize motion resistance"; Journal of Orthopaedic Trauma, 2000, vol. 14, No. 1, pp. 41-47.
Neel, Michael D., M.D et al.; "Early Multicenter Experience With a Noninvasive Expandable Prosthesis"; Clinical Orthopaedics and Related Research, 2003, No. 415, pp. 72-81.
Neel, Michael D., M.D.; "Repiphysis-Limb Salvage System for the Skeletally Immature"; Wright Medical Technology, Reipiphysis Limb Salvage System, 2004, pp. 1-8.
Nockels, Russ P.; "Dynamic Stabilization in the Surgical Management of Painful Lumbar Spinal Disorders"; Spine, 2005, vol. 30, No. 16S, pp. S68-S72.
Orthofix; "Xcaliber Articulated Ankle"; advertising brochure, May 2004.
Orthofix; "Gentle Limb Deformity Correction"; website pages, http://www.eight-plate.com/, 2008.
Perry, Clayton R. et al.; "Patellar Fixation Protected with a Load-Sharing Cable: A Mechanical and Clinical Study"; Journal of Orthopaedic Trauma, 1988, vol. 2, No. 3, pp. 234-240.
Pilliar et al., "Bone Ingrowth and Stress Shielding with a Porous Surface Coated Fracture Fixation Plate," Journal of Biomedical Materials Research, vol. 13, (1979), pp. 799-810.
Repicci, John A., M.D. et al. "Minimally Invasive Unicondylar Knee Arthroplasty for the Treatment of Unicompailmental Osteoarthritis: an outpatient arthritic bypass procedure"; Orthopedic Clinics of North America, 35 (2004), pp. 201-216.
Sharma, Leena et al. "The Mechanism of the Effect of Obesity in Knee Osteoarthritis—The Mediating Role of Malalignment"; Arthritis & Rheumatism, vol. 43, No. 3, Mar. 2000, pp. 568-575.
Sommerkamp, G. et al.; "Dynamic External Fixation of Unstable Fractures of the Distal Part of the Radius"; The Journal of Bone and Joint Surgery; Aug. 1994, vol. 76-A, No. 8, pp. 1149-1161.
Tencer, Allan F. et al. "Fixation of the Patella (Chap. 9.3)"; in: Biomechanics in Orthopedic Trauma Bone Fracture and Fixation, 1994.
Thakur, A.J.; "Tension Band Wiring"; in; The Elements of Fracture Fixation, 1997, pp. 126-146.
Uchikura, C. et al.; "Comparative Study of Nonbridging and Bridging External Fixators from Unstable Distal Radius fractures"; Journal of Orthopaedic Science, 2004, vol. 9, No. 6, pp. 560-565.
Van Der Esch, M. et al.; "Structural Joint Changes, Malalignment, and Laxity in Osteoarthritis of the knee"; Scand J Rheumatol 2005; 34: pp. 298-301.
Weisstein, Jason S., M.D. et al.; "Oncologic Approaches to Pediatric Limb Preservation"; Journal of the American Academy of Orthopaedic Surgeons; vol. 13, No. 8, Dec. 2005, pp. 544-554.
Wilke, Hans-Joachim et al.; "Biomechanical Evaluation of a New Total Posterior-Element Replacement System" Spine, 2006, vol. 31, No. 24, pp. 2790-2796.
Wilkins, Ross M., M.D. et al. "The Phenix Expandable Prosthesis"; Clinical Orthopaedics and Related Research, No. 382, pp. 51-58.
Yamamoto, Ei et al.; "Effects of Stress Shielding on the Transverse Mechanical Properties of Rabbit Patellar Tendons"; Journal of Biomechanical Engineering, 2000, vol. 122, pp. 608-614.
Nagai, et al., "B109 Mobility Evaluation of Hip-Joint Nonweight-Bearing Device," The Japan Society of Mechanical Engineers No. 02-26.

(56) References Cited

OTHER PUBLICATIONS

European Search Report dated Aug. 7, 2014, issued in connection with related EP14164658.
Extended Search Report dated Aug. 26, 2014, issued in connection with related EP14164658.
Non-Final Rejection Office Action dated Aug. 27, 2014, in connection with related U.S. Appl. No. 14/175,813, filed Feb. 7, 2014.
Notice of Allowance dated Aug. 4, 2014 in connection with related U.S. Appl. No. 14/175,829, filed Feb. 7, 2014, Vivek Shenoy.
Office Action dated Dec. 19, 2014, in connection with U.S. Appl. No. 13/843,128, filed Mar. 15, 2013.
Response to Final Office Action dated Apr. 1, 2013, in connection with related U.S. Appl. No. 13/002,829, filed Aug. 27, 2009.
Response to First Non-Final Office Action dated May 5, 2014, in connection with related U.S. Appl. No. 14/175,829, filed Feb. 7, 2014.
Response to Restriction Requirement dated Oct. 27, 2014, issued in connection with related U.S. Appl. No. 13/843,128, filed Mar. 15, 2013.
Restriction Requirement dated Aug. 25, 2014, issued in connection with related U.S. Appl. No. 13/843,128, filed Mar. 15, 2013.
Synthes, Inc., LCP Proximal Tibial Plate 3.5; Technique Guide; pp. 1-20; Jun. 2011.
Synthes TomoFix Osteotomy System Technique Guide. A comprehensive plating system for stable fixation of osteotomies around the knee. 38 pages.
Loqteq Anatomical Plating System Design Rationale. Locking Compression Technology by aap. aap Implantate AG. 11 pages.
Response to Election/Restriction dated Jul. 1, 2014 in connection with related U.S. Appl. No. 14/175,813, filed Feb. 7, 2014.
Office Action dated Oct. 2, 2017, in connection with U.S. Appl. No. 15/295,560, filed Oct. 17, 2016.
Response to Office Action dated Mar. 2, 2018, in connection with U.S. Appl. No. 15/295,560, filed Oct. 17, 2016.
Final Office Action dated Jun. 14, 2018, in connection with U.S. Appl. No. 15/295,560, filed Oct. 17, 2016.
Arnoczky et al., Biomechanical Analysis of Forces Acting About the Canine Hip, American Journal Veterinary Research, vol. 42, Issue: 9, Sep. 1981, pp. 1581-1585.
Becker et al., Surgical Treatment of Isolated Patellofemoral Osteoarthritis, Clinical Orthopaedics and Related Research vol. 466, No. 2, Feb. 2008, pp. 443-449.
Cerejo et al., The Influence of Alignment on Risk of Knee Osteoarthritis Progression According to Baseline Stage of Disease, Arthritis & Rheumatism, vol. 46, No. 10, Oct. 2002, pp. 2632-2636.
Clifford et al., The KineSpring load absorber implant: Rationale, Design and Biomechanical Characterization, Journal of Medical Engineering & Technology, vol. 35, No. 1, Jan. 2011, pp. 65-71.
Delp et al., An Interactive Graphics-Based Model of the Lower Extremity to Study Orthopaedic Surgical Procedures, IiEEE Transactions on Biomedical Engineering, vol. 37, No. 8, Aug. 1990, pp. 757-767.
Delp et al., Biomechanical Analysis of the Chiari Pelvic Osteotomy Preserving Hip Abductor Strength, Reprinted from Clinical Orthopaedics, vol. 25, May 1990, pp. 189-198.
Free et al., Trochanteric Transfer in Total Hip Replacement: Effects on the Moment Arms and Force-Generating Capacities of the Hip Abductors, Journal of Orthopaedic Research, vol. 14, No. 2, 1996, pp. 245-250.
Jack Farr, M.D., Tibial Tubercle Osteotomy, Techniques in Knee Surgery, vol. 2, Issue 1, 2003, pp. 28-42.
Goeiz et al., Hip Joint Contact Force in the Emu (Dromaius novaehollandiae) during Normal Level Walking, Journal of Biomechanics, 41(4), 2008, pp. 770-778.
Jacobsen et al., Hip dysplasia: a significant risk factor for the development of hip osteoarthritis. A cross-sectional survey, Rheumatology vol. 44 No. 2, 2005, pp. 211-218.

Jingushi et al., Transtrochanteric Valgus Osteotomy for the Treatment of Osteoarthritis of the Hip Secondary to Acetabular Dysplasia, The Journal of Bone & Joint Surgery [Br], vol. 84-B, No. 4, May 2002, pp. 535-539.
Kirkley et al., The Effect of Bracing on Varus Gonarthrosis, The Journal of Bone and Joint Surgery, vol. 81-A, No. 4, Apr. 1999, pp. 539-548.
Lafeber et al., Unloading Joints to Treat Osteoarthritis, including Joint Distraction, Current Opinion in Rheumatology 2006,18, pp. 519-525.
Lloyd et al., An EMG-driven Musculoskeletal Model to Estimate Muscle Forces and Knee Joint Moments in Vivo, Journal of Biomechanics 36, 2003, pp. 765-776.
Lloyd et al., Strategies of Muscular Support of Varus Andvalgus Isometric Loads at the Human Knee, Journal of Biomechanics 34, 2001, pp. 1257-1267.
Maquet, P, Biomechanics of Hip Dysplasia, Acta Ortopaedica Belgica, vol. 65-3, 1999, pp. 302-314.
McWilliams et al., Mild Acetabular Dysplasia and Risk of Osteoarthritis of the hip: a case-control study, Annals of the Rheumatic Diseases, 2010; 69, pp. 1774-1778.
Merritt et al., Influence of Muscle-Tendon Wrapping on Calculations of Joint Reaction Forces in the Equine Distal Forelimb, Journal of Biomedicine and Biotechnology, vol. 2008, Article ID 165730, 9 pages.
Pedersen et al., A Model to Predict Canine Pelvic Limb Musuloskeletal Geometry, Acta Anat 1991; 140, pp. 139-145.
Pollo et al., Knee Bracing for Unicompartmental Osteoarthritis, Journal of the American Academy of Orthopaedic Surgeons, vol. 14, No. 1, Jan. 2006, pp. 5-11.
Pollo et al., Reduction of Medial Compartment Loads with Valgus Bracing of the Osteoarthritic Knee, The American Journal of Sports Medicine, vol. 30, No. 3, 2002, pp. 414-421.
Saleh et al., Operative Treatment of Patellofemoral Arthritis, The Journal of Bone & Joint Surgery, vol. 87-A, No. 3, Mar. 2005, pp. 659-671.
Sharma et al., The Role of Knee Alignment in Disease Progression and Functional Decline in Knee Osteoarthritis, JAMA, vol. 286, No. 2, Jul. 11, 2001, pp. 188-195.
Sims et al., Investigation of Hip Abductor Activation in Subjects with Clinical Unilateral Hip Osteoarthritis, Annals of the Rheumatic Diseases, 2002; 61: pp. 687-692.
Thorp et al., The biomechanical effects of focused muscle training on medial knee loads in OA of the knee: a pilot, proof of concept study, Journal of Musculoskeletal and Neuronal Interactions, 10(2): 2010, pp. 166-173.
Wenger et al., Early Surgical Correction of Residual Hip Dysplasia: The San Diego Children's Hospital Approach, Acta Orthopaedica Belgica, vol. 65, 1999, pp. 277-287.
Winby et al., Muscle and External Load Contribution to Knee Joint Contact Loads during Normal Gait, Journal of Biomechanics 42, 2009, pp. 2294-2300.
Response to Final Office Action dated Apr. 1, 2013, in connection with related U.S. Appl. No. 13/002,829 International filing date Aug. 27, 2010.
Amendment and Response to Final Office Action dated May 20, 2013, in connection with related U.S. Appl. No. 12/870,462, filed Aug. 27, 2010.
Advisory Action dated Apr. 23, 2013 in connection with related U.S. Appl. No. 13/002,829, filed Jan. 6, 2011.
Advisory Action dated Jun. 20, 2013 in connection with related U.S. Appl. No. 13/002,829, filed Jan. 6, 2011.
Tew, M et al.; Anteriorization of the quadriceps tendon. A biomechanical study on a new technique for unloading the patellofemoral joint. University of Tennessee College of Medicine; Poster No. 0848 • ORS 2012 Annual Meeting.
Miller, R.K., Goodfellow, J.W., Murray, D.W. and O'Connor, J.J., In vitro measurement of patellofemoral force after three types of knee replacement; The Journal of Bone & Joint Surgery (Br), vol. 80-B, No. 5, Sep. 1998; pp. 900-906.
Ganesh, V.K., et al., Biomechanics of bone-fracture fixation by stiffness-graded plates in comparison with stainless-steel plates, Biomedical Engineering Online, 2005, 4:46, 15 pgs.

(56) References Cited

OTHER PUBLICATIONS

Benli, Semih et al., Evaluation of bone plate with low-stiffness material in terms of stress distribution, Journal of Biomechanics, 41 (2008) 3229-3235.
Haase, Kristina et al., A Discussion on Plating Factors that Affect Stress Shielding Using Finite Element Analysis, Journal of Biomechanical Science and Engineering, vol. 5, No. 2, 2010, p. 129.
Anatomic Locked Plating System Brochure, BIOMET® Orthopedics, Form BMET0002.0, Rev 053112, pp. 1-16, Copyright 2012.
SPS Periarticular Plates Brochure, STRYKER® Trauma AG, Literature No. 982274, Lot B46404, pp. 1-8; Copyright 2004.
Zimmer® Periarticular Distal Femoral Locking Plate Surgical Technique, the Science of the Landscape, ZIMMER, 97-2347-044-00 Rev. 1 7.5 ML; pp. 1-20; Copyright 2005.
Hessmann et al., Compression Plate With or Without Lag Screw; AO Surgery Reference—Online reference in clinical life; Distal Tibia—Reduction & Fixation—Compression Plate; https://www2.aofoundation.org/wps/portal; pp. 1-9 Dec. 3, 2008.
LCP Locking Compression Plate—Ordering Information; SYNTHES®, 036.000.017, SE_042064 AD, 31080015; pp. 1-68; Copyright 2008.
Plates for 4.5 mm and 6.5 mm Screws; Raj Surgical Works; http://www.orthoindustries.com/plates-for-4-5-mm-and-6-5-mm-screws.html; pp. 1-8; printed Nov. 19, 2012.
Final (Rejection) Office Action dated Mar. 18, 2013, in connection with related U.S. Appl. No. 12/870,462, filed Aug. 27, 2010.
Final Office Action dated Jan. 31, 2013, in connection with related U.S. Appl. No. 13/002,829, filed Jan. 6, 2011.
PCT International Search Report and Written Opinion dated Jan. 9, 2014, for related application PCT/US2013/058877 filed Sep. 10, 2013 entitled "Method and Apparatus for Treating Canine Cruciate Ligament Disease," Vivek Shenoy.
Bruce et al., "Patellar Contact Pressure Changes with Anteromedialization of Tibial Tubercle, Lateral Release, and New Technique for Elevating Quadriceps Tendon: A Biomechanical Study," Journal of Surgical Orthopaedic Advances 22(4), pp. 270-276, 2013.
Notice of Allowance dated Feb. 3, 2015, in connection with related U.S. Appl. No. 14/175,813, filed Feb. 7, 2014.
Non-Final Office Action dated Apr. 11, 2014, in connection with related U.S. Appl. No. 14/175,829, filed Feb. 2, 2014, Vivek Shenoy.
Final Office Action dated Feb. 26, 2015, in connection with related U.S. Appl. No. 13/002,829, filed Jan. 6, 2011.
Response to Non-Final Office Action dated May 26, 2015, in connection with related U.S. Appl. No. 13/002,829, filed Jan. 6, 2011.
Response to Non-Final Office Action dated Apr. 20, 2015, in connection with related U.S. Appl. No. 13/843,128, filed Mar. 15, 2013.
Final Office Action dated Jun. 10, 2015, in connection with related U.S. Appl. No. 13/843,128, filed Mar. 15, 2013.
Partial International Search dated May 11, 2015, in connection with related PCT/US2015/019938, filed Mar. 11, 2015.
International Search Report and Written Opinion dated Jul. 3, 2015, in connection with related PCT/US2015/019938, filed Mar. 11, 2015.
Office Action dated Jul. 1, 2015, in connection with related U.S. Appl. No. 13/974,930, filed Aug. 23, 2013.
Restriction Requirement dated Jul. 23, 2015, in connection with related U.S. Appl. No. 14/642,121, filed Mar. 9, 2015.
Response to Final Office Action dated Aug. 10, 2015, in connection with related U.S. Appl. No. 13/843,128, filed Mar. 15, 2013.
Response to Restriction Requirement dated Sep. 23, 2015, in connection with related U.S. Appl. No. 14/642,121, filed Mar. 9, 2015.
Supplemental Response to Final Office Action dated Sep. 3, 2015, in connection with related U.S. Appl. No. 13/843,128, filed Mar. 15, 2013.
Final Office Action dated Sep. 15, 2015, in connection with related U.S. Appl. No. 13/002,829, filed Jan. 6, 2011.
Chow, S. P. et al., Fracture of the Tibial Tubercle in the Adolescent; British Editorial Society of Bone and Joint Surgery, vol. 72-B. No. 2, Mar. 1990.
Response to First Non-Final Office Action dated Nov. 2, 2015, in connection with U.S. Appl. No. 13/974,930, filed Aug. 23, 2013.
Non-Final Office Action dated Oct. 7, 2015, in connection with U.S. Appl. No. 14/642,121, filed Mar. 9, 2015.
Gumpel et al., An Objective Assessment of Synovitis of the Knee: Measurement of the Size of the Suprapatellar Pouch on Xeroradiography Annals of the Rheumatic Diseases. 1980, (39): 359-366.
Response to First Non-Final Office Action dated Jan. 25, 2016, in connection with related U.S. Appl. No. 14/642,121, filed Mar. 9, 2015.
Office Action dated Feb. 26, 2016, in connection with related U.S. Appl. No. 13/974,930, filed Aug. 23, 2013.
Appellant's Brief dated Mar. 15, 2016, in connection with related U.S. Appl. No. 13/002,829, filed Jan. 3, 2011.
Lafaver, et al., "Tibial Tuberosity Advancement for Stabilization of the Canine Cranial Cruciate Ligament-Deficient Stifle Joint: Surgical Technique, Eady Results, and Complications in 101 Dogs", Veterinary Surgery, 36:573-586, 2007.
Office Action dated May 5, 2016, in connection with U.S. Appl. No. 14/642,121, filed Mar. 9, 2015, Shenoy.
Examination Search Report dated Sep. 6, 2016, in connection with Canadian Application No. 2,771,332.
Response to Second Non-Final Office Action dated Oct. 5, 2016, in connection with U.S. Appl. No. 14/642,121, filed Mar. 9, 2015, Shenoy.
Notice of Allowance dated Jun. 21, 2016, in connection with U.S. Appl. No. 13/974,930, filed Aug. 23, 2013, Shenoy.
Restriction Requirement dated Jul. 22, 2015, in connection with related U.S. Appl. No. 14/644,792, filed Mar. 11, 2015.
Response to Restriction Requirement dated Sep. 11, 2015, in connection with related U.S. Appl. No. 14/644,792, filed Mar. 11, 2015.
Non-final Office Action dated Sep. 25, 2015, in connection with related U.S. Appl. No. 14/644,792, filed Mar. 11, 2015.
Office Action dated May 18, 2016, in connection with U.S. Appl. No. 14/644,792, filed Mar. 11, 2015, Shenoy.
Amendment and Response to Second Non-Final Office Action dated Sep. 19, 2016, in connection with U.S. Appl. No. 14/644,792, filed Mar. 11, 2015, Shenoy.
Office Action dated Oct. 6, 2016, in connection with U.S. Appl. No. 13/002,829, filed Jan. 6, 2011, Shenoy.
Response to Final Office Action dated Apr. 26, 2016, in connection with U.S. Appl. No. 13/974,930, filed Aug. 23, 2013.
Amendment and Response to First Non-Final Office Action dated Feb. 3, 2016, in connection with U.S. Appl. No. 14/644,792, filed Mar. 11, 2015, Shenoy.
Response to Final Office Action dated Apr. 26, 2016, in connection with U.S. Appl. No. 13/974,930, filed Aug. 23, 2013, Shenoy.
PCT International Search Report and Written Opinion dated Oct. 20, 2010, for related application PCT/US2010/046996 filed Aug. 27, 2010 entitled "Method and Apparatus for Force Redistribution in Articular Joints" Vivek Shenoy, Mark Deem and Hanson Gifford.
Office Action dated May 17, 2012, in connection with related U.S. Appl. No. 13/002,829, filed Jan. 6, 2011, Shenoy.
Office Action dated Jul. 24, 2012, in connection with related U.S. Appl. No. 12/870,462, filed Aug. 27, 2010, Shenoy.
Final (Rejection) Office Action dated Jan. 31, 2013, in connection with related U.S. Appl. No. 13/002,829, filed Jan. 6, 2011.
Office Action dated Jul. 9, 2012, in connection with related European Application No. 10812664, entitled Method and Apparatus for Force Redistributon in Articular Joints, filed Aug. 27, 2010, Cotera, Inc.
Maquet, P., Biomechanical Treatment of Patellofemoral Osteoarthritis. Advancement of the Patellar Tendon; Review of Rheumatism and Osteoarticular Diseases, National Library of Medicine, Dec. 1963, vol. 30, Issue 12, pp. 780-785.
Maquet, Paul G.J., Biomechanics of the Knee With Application to the Pathogenesis and the Surgical Treatment of Osteoarthritis; Springer-Verlag Berlin Heidelberg New York, 1976, pp. 134-204.

(56) References Cited

OTHER PUBLICATIONS

Sridhar et al., Obesity and symptomatic osteoarthritis of the knee, The Journal of Bone & Joint Surgery, Instructional Review, vol. 94-B, No. 4, Apr. 2012, pp. 433-441.
Lasmar, et al., Importance of the Different Posterolateral Knee Static Stabilizers: Biomechanical Study; Clinics 2010; 65(4) pp. 433-440.
Hunter, David et al., Alignment and Osteoarthritis of the Knee, Journal of Bone and Joint Surgery, 2009: 91 Suppl. 1:85-9, pp. 85-89.
Halbrecht, Jeffrey L., Arthroscopic Patella Realignment: An All-Inside Technique, Arthroscopy: The Journal of Arthroscopic and Related Surgery, vol. 17, No. 9 (Nov.-Dec. 2001; pp. 940-945.
Arnold, Allison S., et al., Do the hamstrings operate at increased muscle-tendon lengths and velocities after surgical lengthening? Journal of Biomechanics, Mar. 2005; pp. 1-9.
Unnanuntana, Aasis et al., Management of chronic lateral instability due to lateral collateral ligament deficiency after total knee arthroplasty: a case report; Journal of Medical Case Reports, 2010, 4:144; p. 1-5.
Maquet, P., Biomechanical Aspects of the Relationship between Femur and Patella, Z. Orthop. 112 (1974); pp. 620-623.
Kwak, et al., Hamstrings and Iliotibial Band Forces Affect Knee Kinematics and Contact Pattern, Journal of Orthopaedic Research, 18: 101-108; The Journal of Bone and Joint Surgery, Inc. 1999.
Maquet P., Reduction of the articular pressure of the hip by surgical lateralization of the greater trochanter, PMID: 1015273, Clin Orthop Relat Res. 1977, Mar.-Apr.; (123): 138 (Abstract only).
Maquet P., Importance of the position of the greater trochanter, PMID: 2382566, Acta Orthop Belg. 1990; 56 (1 Pt. B): 307 (Abstract only).
Maquet, Paul, "Advancement of the Tibial Tubersosity," Clinical Orthopaedics and Related Research, No. 15, 1976, pp. 225-230.
Townsend et al., "The Biomechanics of the Human Patella and its Implications for Chodromalacia," Journal of Biomechanics, 1977, vol. 10, pp. 403-407.
Supplementary European Search Report dated May 23, 2012 for related application EP10812664 filed Aug. 27, 2010, entitled "Method and Apparatus for Force Redistribution in Articular," Cotera, Inc.

* cited by examiner

METHOD AND APPARATUS FOR TREATING CANINE CRUCIATE LIGAMENT DISEASE

RELATED APPLICATIONS

This application is a continuation of U.S. Nonprovisional patent application Ser. No. 13/002,829, filed on Mar. 9, 2015, and titled "Method and Apparatus for Treating Canine Cruciate Ligament Disease", which application was a continuation of International Patent Application No. PCT/US2013/058877, filed Sep. 10, 2013, and titled "Method and Apparatus for Treating Canine Cruciate Ligament Disease", which claims the benefit of priority of U.S. Provisional Patent Application Ser. No. 61/699,089, filed Sep. 10, 2012, and titled "Method and Apparatus for Treating Canine Cruciate Ligament Disease"; U.S. application Ser. No. 13/002,829 was also a continuation-in-part of U.S. Nonprovisional patent application Ser. No. 13/002,829, filed Aug. 27, 2010, and titled "Method and Apparatus for Force Redistribution in Articular Joints"; which application was a 371 of International Patent Application No. PCT/US10/46996, filed Aug. 27, 2010, and titled "Method and Apparatus for Force Redistribution in Articular Joints", which claims the benefit of priority of U.S. Provisional Patent Application Ser. No. 61/237,518, filed Aug. 27, 2009, and U.S. Provisional Patent Application Ser. No. 61/288,692, filed Dec. 21, 2009, each entitled "Method and Apparatus for Force Redistribution in Articular Joints." Each of the foregoing applications is incorporated by reference herein in its entirety.

FIELD OF THE INVENTION

The present invention generally relates to the field of veterinary orthopedic disease. In particular, the present invention is directed to an interventional technique and an implant for treating canine cruciate ligament disease.

BACKGROUND

Cruciate ligament degeneration or rupture is a common canine disease. The cruciate ligaments are the primary stabilizing structures of canine stifle joint. The canine stifle joint is condylar synovial joint. The primary motion of joint is flexion and extension. The three major muscles comprising the caudal thigh group are the biceps femoris, the semitendinosus and the semimembranosus, also collectively known as the hamstring muscles. The bones, muscles, tendons, ligaments etc. of the canine stifle joint are shown in detail in FIGS. 1-6 (Reference: Carpenter, D. H. et al, Mini Review of Canine Stifle Joint Anatomy, *Anat. Histol. Embryol.*, 29, 321-329, 2000).

A cranial view of the left stifle showing associated ligaments and structures is shown in FIG. 1. The following features are identified: 1A, femoral trochlea; 2A, lateral ridge of femoral trochlea; 3A, tendon of long digital extensor; 4A, tendon of popliteus; 5A, lateral collateral ligament; 6A, lateral meniscus; 7A, tibial tuberosity; 8A, patellar ligament; 9A, patella; 10A, parapatellar fibrocartilage; 11A, intermeniscal ligament; 12A, medial meniscus; 13A, medial collateral ligament; 14A, cranial cruciate ligament; 15A, caudal cruciate ligament; 16A, medial ridge of the trochlea.

A caudal view of the right stifle showing associated ligaments and structures is shown in FIG. 2. The following features are identified: 1B, cranial cruciate ligament; 2B, lateral collateral ligament, 3B, lateral meniscus; 4B, cranial ligament of the fibular head; 5B, caudal ligament of the fibular head; 6B, fibula; 7B, caudal meniscotibial ligament of the lateral meniscus; 8B, caudal cruciate ligament; 9B, medial meniscus; 10B, medial collateral ligament; 11B, meniscofemoral ligament.

A lateral view of the right stifle showing associated ligaments and structures is shown in FIG. 3. The following features are identified: 1C, popliteus tendon; 2C, lateral collateral ligament; 3C, sesamoid; 4C, lateral femoropatellar ligament; 5C, quadriceps muscle group tendon of insertion; 6C, patella; 7C, patellar ligament; 8C, lateral meniscus; 9C, tibial tuberosity; 10C, tibial crest; 11C, long digital extensor tendon of origin; 12C, cranial ligament of fibular head; 13C, fibula; 14C, tibia; 15C, os femoris.

A medial view of the right stifle showing associated ligaments and structures is shown in FIG. 4. The following features are identified: 1D, os femoris; 2D, medial femoropatellar ligament; 3D, sesamoid; 4D, medial collateral ligament; 5D, popliteus tendon of origin; 6D, cranial ligament of the fibular head; 7D, fibula; 8D, tibia; 9D, tibial crest; 10D, tibial tuberosity; 11D, patellar ligament; 12D, medial meniscus; 13D, patella; 14D, quadriceps muscle group tendon of insertion.

A medial view of the left pelvic limb muscles and associated structures is shown in FIG. 5. The following features are identified: 1E, cranial sartorius; 2E, caudal sartorius; 3E, cranial tibial; 4E, deep digital flexor; 5E, tibia; 6E, common calcanean tendon; 7E, superficial digital flexor; 8E, gastrocnemius; 9E, biceps femoris tendon of insertion; 10E, semitendinosus, 11E, gracilus; 12E, pectineus; 13E, vastus medialis; 14E, adductor magnus et brevis; 15E, semimembranosus.

A lateral view of the right pelvic limb muscles and associated structures is shown in FIG. 6. The following features are identified: 1F, middle gluteal; 2F, tensor fasciae latae; 3F, cranial sartorius; 4F, vastus lateralis; 5F cranial tibial; 6F, gastroenemiius; 7F, superficial digital flexor; 8F, long digital extensor; 9F, common calcanean tendon; 10F, biceps femoris tendon of insertion; 11F, caudal head of biceps femoris; 12F, cranial head of biceps femoris; 13F, semitendinosus; 14F, semimembranosus; 15F, superficial gluteal.

The cranial cruciate ligament (CrCL) prevents cranial tibial translation or the tibial forward thrust, limits excessive internal rotation of the tibia and prevents hyper extension of the stifle. During the stance phase (weight bearing phase) of the gait cycle, loading of the stifle joint leads to a ventrally directed compressive force, and a horizontally directed force, or a cranial tibial thrust. In an intact stifle, the CrCL resists this force, minimizing any cranial translation of the tibia. In a CrCL deficient stifle, the lack of the stabilizing force, leads to cranial translation of the tibia during the weight bearing phase of the gait cycle. The translation of the tibia during the stance phase can alter the load distribution within the stifle joint, leading to pain, stiffness and osteoarthritis of the joint.

Common surgical treatment options for cruciate ligament disease are Tibial Plateau Levelling Osteotomy (TPLO) and Tibial Tuberosity Advancement (TTA). In a TPLO surgery, illustrated in FIG. 7, a semi-circular cut is made on the dorsal end of the tibia. The tibial articular surface is then rotated and stabilized using bone plates and screws. By levelling the tibial plateau, cranial slippage of the tibia during the stance phase is prevented. In a TTA surgery, illustrated in FIG. 8, the attachment site of the patellar tendon to the tibia is moved forward by cutting the tibial tuberosity and repositioning it with bone plates and screws.

TPLO and TTA both carry a risk of failure due to poor bone healing after the osteotomy, as well as a risk of failure due to fracture of the bone weakened by the osteotomy. Moreover, these surgeries require significant pain management following surgery and entail long recovery times.

SUMMARY OF DISCLOSURE

Exemplary methods disclosed herein comprise selecting at least one of the muscles and connective tissues associated with the canine stifle joint as target tissue for treatment, and displacing the target tissue without severing the bones or target tissue, thereby achieving a therapeutic effect. In exemplary embodiments described herein, the target tissue is displaced by placing an implant in contact with the target tissue and displacing the target tissue to reduce cranial tibial thrust. The implant may be secured to a bone and/or to soft tissues, which may include the target tissue. In a preferred embodiment, the capsule surrounding the joint is not penetrated. Implants may be secured variously on medial, lateral, caudal or cranial sides of the femur or the tibia to displace target connective tissue or muscle comprising at least one of the quadriceps muscle or tendon, the patellar tendon, the biceps femoris muscle or tendon, or the semi-tendinous muscle or tendon. Displacement may be in the caudal or cranial direction relative to the bone on which the implant is placed. The implant may be completely outside the capsule surrounding the stifle joint or may be in contact with the exterior of the capsule.

In one implementation, the present disclosure is directed to a method for treating canine cruciate ligament disease. The method includes securing an implant to one of the canine femur or tibia and reducing cranial tibial thrust by displacing connective tissue or muscle acting on the canine stifle joint with the implant, wherein the displacing comprises displacing the hamstring muscles caudally.

In another implementation, the present disclosure is directed to a method for treating canine cruciate ligament disease. The method includes securing an implant to one of the canine femur or tibia outside of the capsule surrounding the stifle joint, positioning a displacement portion of the implant under the hamstring muscles, and displacing the hamstring muscles caudally with the displacement portion to reposition the hamstring muscles greater than about 2 mm up to about 25 mm beyond the natural anatomical track of the hamstring muscles.

In yet another implementation, the present disclosure is directed to a device for treating canine cruciate ligament disease. The device includes an implant configured and dimensioned to be secured to one of the canine femur or tibia and to extend under a target tissue, the target tissue comprising at least one connective tissue or muscle of the stifle joint including at least the hamstring muscles, to displace the target tissue sufficiently to reduce cranial tibial thrust, wherein the implant comprises a fixation portion configured to be secured to one the bone, and a displacement portion extending from the fixation portion and configured to atraumatically contact and displace the hamstring muscles caudally.

In still another implementation, the present disclosure is directed to an implant for treating canine cruciate ligament disease. The implant includes a fixation portion configured and dimensioned to be secured to a fixation site on one of the canine femur or tibia, a displacement portion configured and dimensioned to extend under and caudally displace the hamstring muscles from a natural anatomical track, the displacement being sufficient to reduce cranial tibial thrust, a bearing surface in the displacement portion, the bearing surface a smooth surface free of discontinuities to atraumatically engage and displace the hamstring muscles, and a spanning section extending between the fixation portion and the displacement portion, the spanning section being configured to position the displacement portion and bearing surface under the hamstring muscles with the fixation portion secured to the fixation site.

By using the implants of the invention, appropriately sized and positioned as described herein, displacement of targeted connective and muscle tissues surrounding the joint is accomplished in order to realign force vectors and/or alter moment arms loading the joint to achieve therapeutic effects without cutting bone and with minimal cutting of the connective tissues. Alternative and more specific devices and methodologies are described in more detail herein below.

BRIEF DESCRIPTION OF DRAWINGS

For the purpose of illustrating the invention, the drawings show aspects of one or more exemplary embodiments of the invention. However, it should be understood that the present invention is not limited to the precise arrangements and instrumentalities shown in the drawings, wherein.

DETAILED DESCRIPTION

Figure 1:
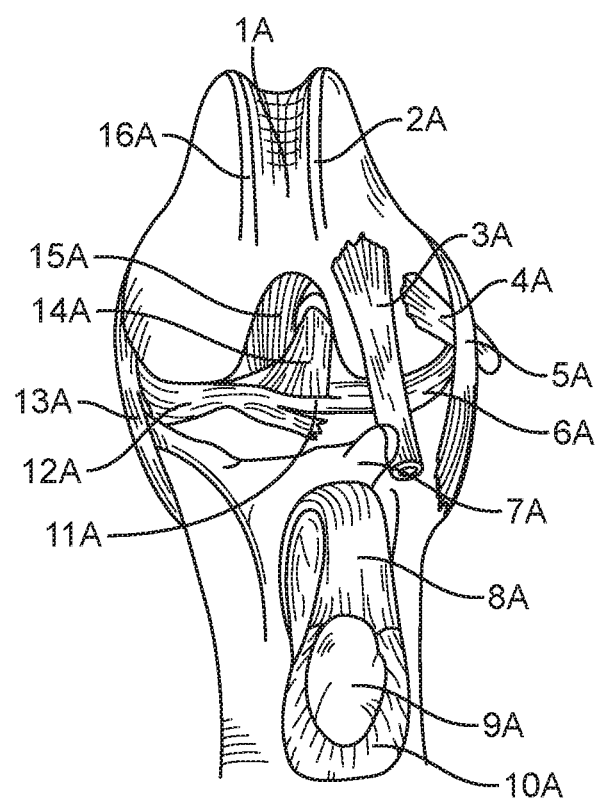
FIG. 1 is the cranial view of a left canine stifle joint showing ligaments and associated structures.
Figure 2:
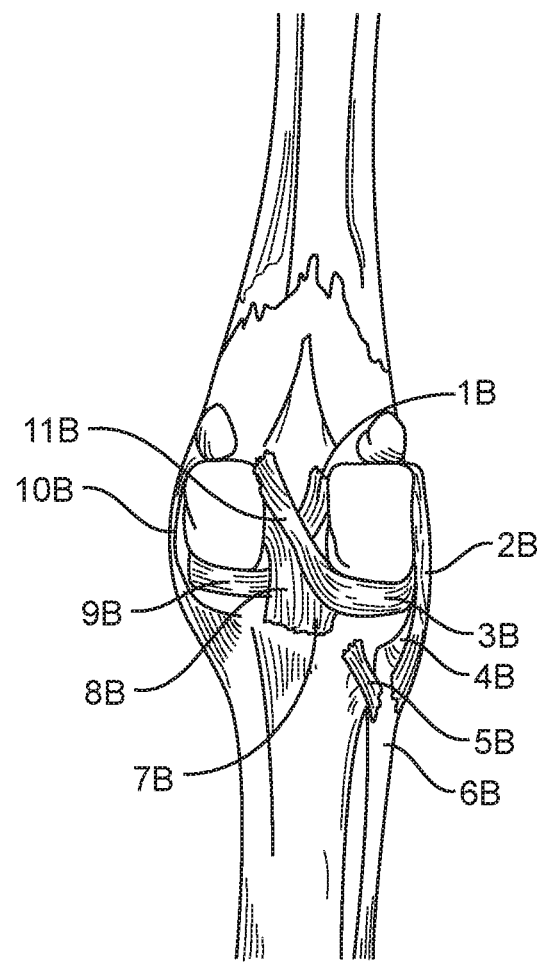
FIG. 2 is the caudal view of a right canine stifle joint showing ligaments and associated structures.
Figure 3:
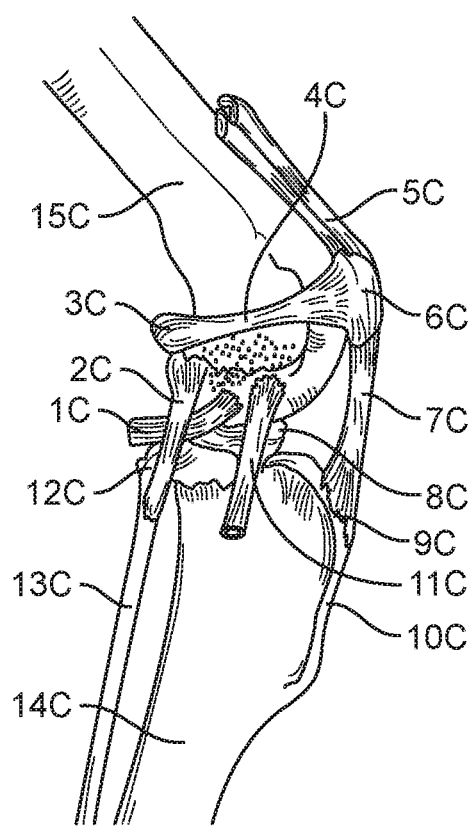
FIG. 3 is the lateral view of a right canine stifle joint showing ligaments and associated structures.
Figure 4:
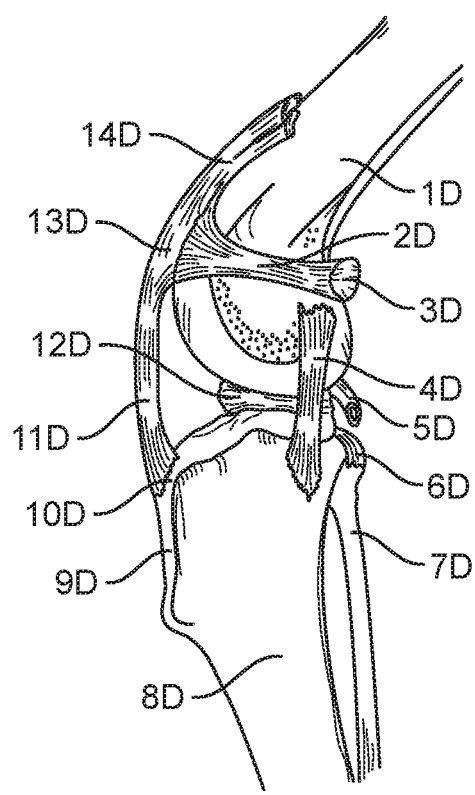
FIG. 4 is the medial view of a right canine stifle joint showing ligaments and associated structures.
Figure 5:
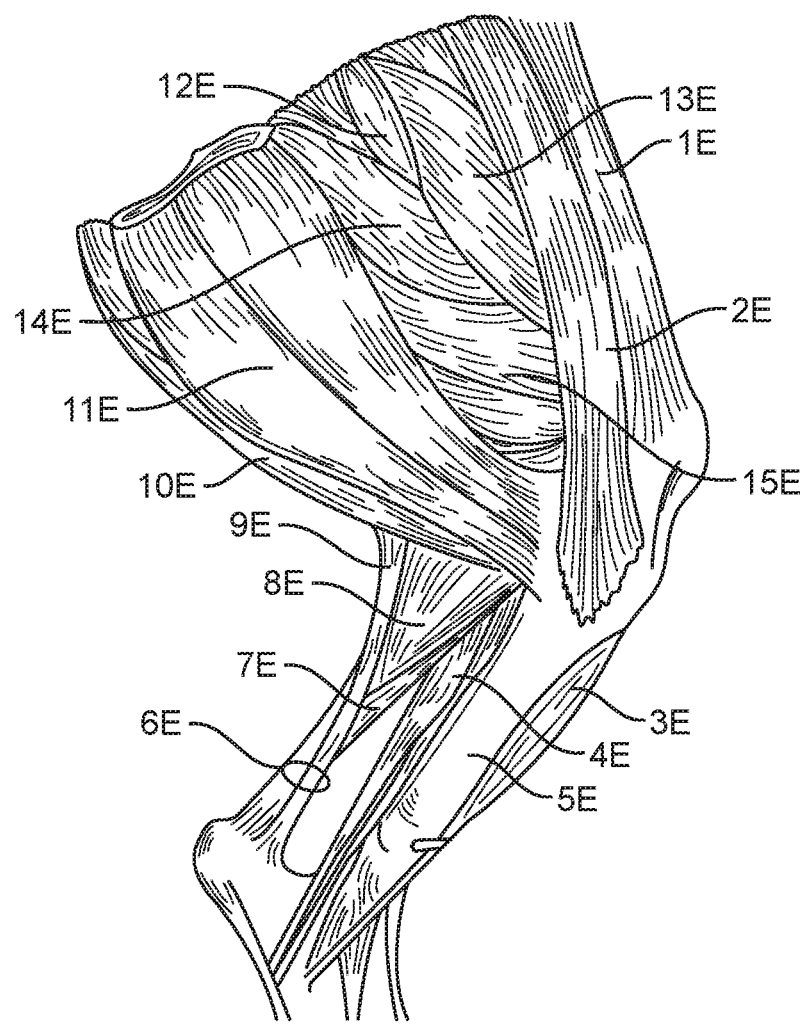
FIG. 5 is the medial view of a left canine pelvic limb showing muscles and associated structures.
Figure 6:
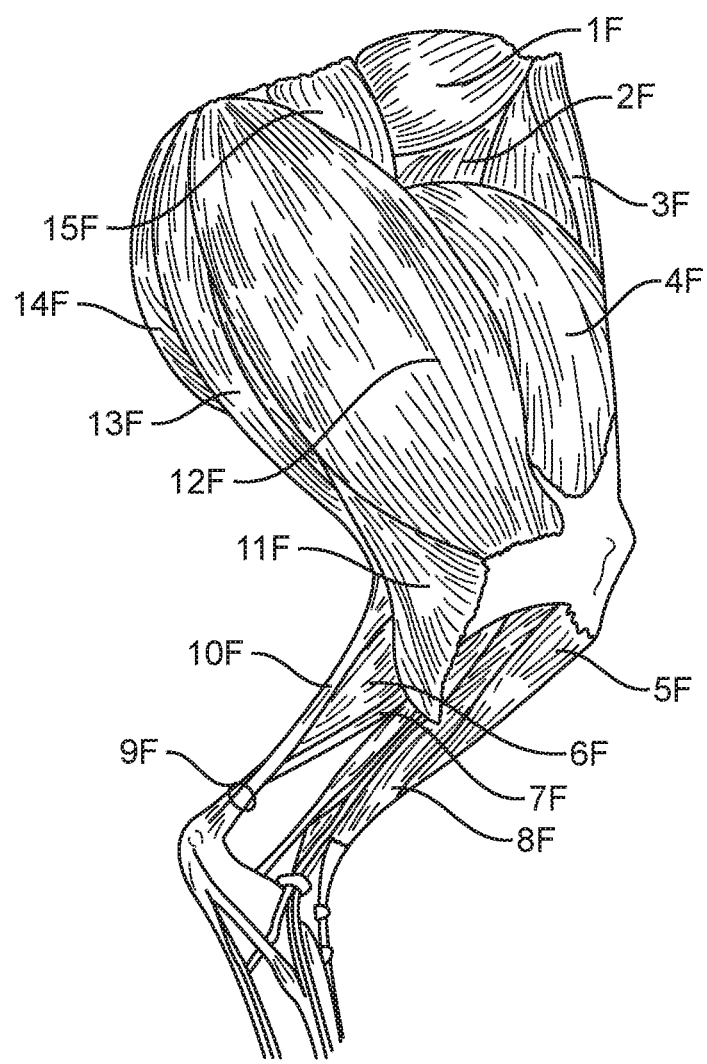
FIG. 6 is the lateral view of a right canine pelvic limb showing muscles and associated structures.
Figure 7:
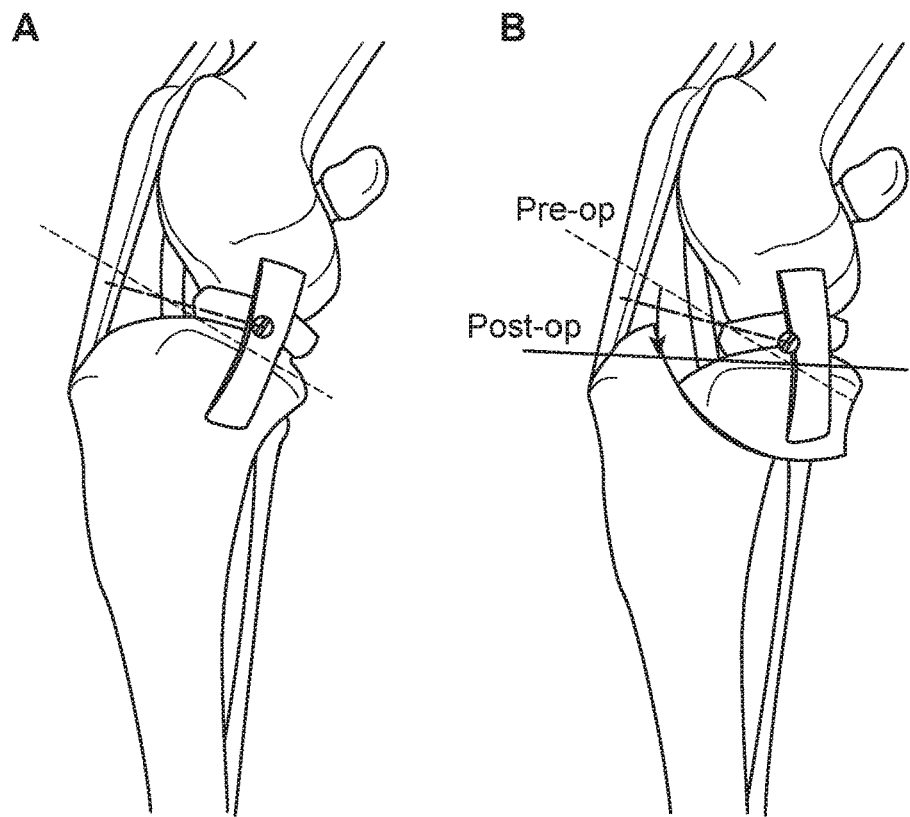
FIG. 7 is a schematic representation of Tibial Plateau Levelling Osteotomy.
Figure 8:
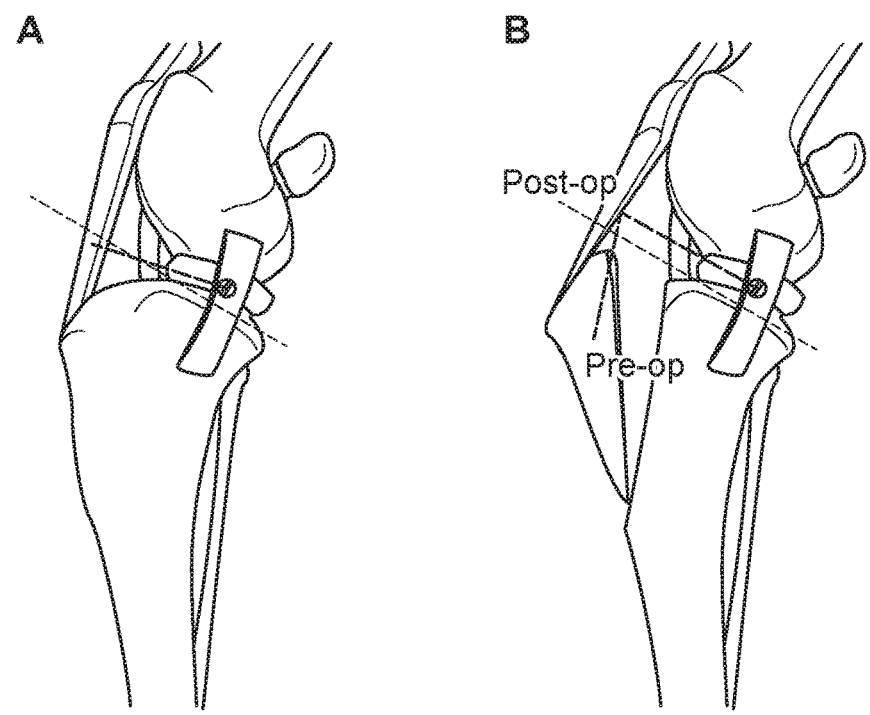
FIG. 8 is a schematic representation of Tibial Tuberosity Advancement osteotomy.

Utilizing embodiments of the present invention, joint conditions that result from or exacerbate unbalanced force distribution through the joint may be addressed by interventional techniques involving a redistribution of forces exerted on the joint without the need for highly invasive surgeries requiring significant trauma to the joint and associated muscle and connective tissues. Redistribution of forces within the target joint in accordance with embodiments described herein may thus provide pain relief or slow down articular cartilage degeneration or enhance cartilage regeneration.

In some embodiments of the invention, increased forces can be selectively applied to one side of a joint by routing select muscle, tendons, ligaments, and/or other connective tissues (target tissues) around a longer, curved, or more angled path, thus increasing the magnitude, altering the effective direction, and/or changing the moment arm of forces exerted by such muscles or tissues on the joint. This may be accomplished, for example, by appropriately shaped implants that may be positioned to displace selected target tissues relatively non-invasively compared to current surgical techniques for addressing such conditions. The amount of displacement of the target tissue may not need to be large in order to provide a substantial therapeutic effect on the target joint. Depending upon the nature of the disease and the size and geometry of the particular canine joint, displacements of greater than about 2 mm up to about 25 mm may be sufficient, with displacements in the range of about 3 mm to about 20 mm also suitable, or more specifically about 4-15 mm.

Exemplary embodiments of the invention described herein are particularly directed to treatment of canine cruciate ligament disease, although the principles of the invention may be applied to other canine or human articular joints as described in the above identified related applications of the present provisional application, which as stated above are incorporated by reference herein. In general, it will be appreciated by persons of ordinary skill in the art that specific features described in connection with one exemplary embodiment may be incorporated in other exemplary embodiments unless otherwise noted. The exemplary embodiments described are thus included to illustrate features of the invention, not limit it.

As used herein, "therapeutic effect" means an effect on a treated joint that reduces forces acting on the articular surfaces, reduces abnormal motion of the bones during flexion/extension, reduces wear, lessens pain or provides another positive outcome for the patient whether across the joint as a whole or in particular parts of the joint. In the canine stifle joint, therapeutic effect would generally be associated with a reduction in cranial tibial thrust. "Therapeutic effect," however, does not imply, and should not be understood as requiring, any specific, quantified outcome other than as stated above.

As used herein, dorsal means directed towards the back, ventral means directed towards the belly, medial means directed towards the mid-line, lateral means directed away from the mid-line towards the flank, cranial means directed towards the cranium (head) and caudal towards the tail. Proximal refers to the end of a structure nearest a major point of reference and distal to the end furthest from a point of reference. The point of reference is usually the origin of a structure (such as a limb). Dorsal plane is parallel to the back, transverse plane is perpendicular to the long axis of the body and sagittal plane divides the body into right/left parts.

Figure 9:
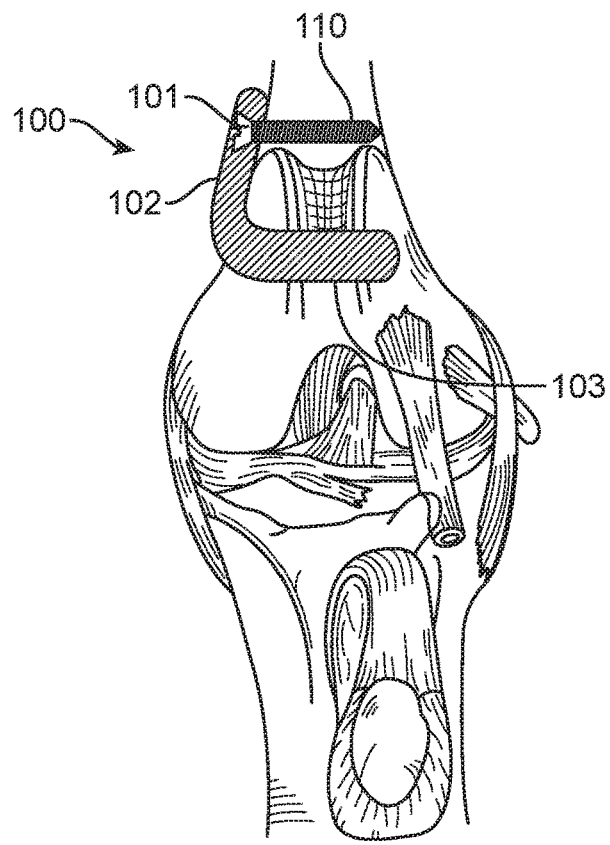
FIG. 9 is a cranial view of a left canine stifle joint illustrating positioning of an exemplary embodiment of the present invention for treating cruciate ligament disease.

Implants according to embodiments of the present invention may be configured and secured in a variety of ways as described below in more detail with respect to exemplary embodiments. However, in general, and with reference to implant 100 shown in FIG. 9, prostheses or implants according to embodiments of the invention may comprise a fixation portion 101 configured to be secure to the bone at a specific location, and which may provide means for securing or anchoring the prosthesis, such as holes for bone screws 110, and a displacement portion 103 configured and dimensioned to displace the target tissue(s) from a pretreatment path as described herein. Other means for securing the fixation portion may include bone ingrowth surfaces, barbs, bone cement, features for fastening sutures or wires, and other devices known in the art for securing implants to bone. The fixation and displacement portions may be separated by a spanning section 102 configured and dimensioned to position the displacement portion with respect to the fixation portion as appropriate to accommodate the anatomical structures at the location of treatment and fixation. For example, the spanning section may be configured to avoid tendon attachment sites between the fixation and displacement region. The displacement portion 102 may be provided with a bearing member for engaging the target tissue, which may be the same or a different material than the underlying substrate.

Depending on the mechanical load on the implant, and the choice of material or materials used to fabricate the implant, thickness of the fixation portion. The thickness of the fixation portion of the implant may be uniform throughout the implant or may vary across the implant. Regions of the fixation portion under higher mechanical load may be thicker than regions under lower mechanical loads. The thickness of the fixation region may also be selected to ensure that the screw-heads used to fix the implant do not protrude over the surface of the implant.

The spanning section may have thickness similar to that of the fixation portion. Persons of ordinary skill in the art will appreciate that a principal consideration for spanning section is sufficient structural integrity to maintain the displacement portion at the desired treatment position. In the displacement portion, displacement distance and thickness may be considered separately. Displacement distance is the distance by which the bearing surface of the displacement portion displaces the target tissue beyond the natural anatomical track of the target tissue, in other words, the displacement of tissue created by the implant. Depending on the particular geometry of the implant, the thickness of the displacement portion may or may not be related to the displacement distance.

In alternative embodiments, components of the prosthesis may be a compliant material such as an elastomer, capsules filled with water, saline, silicone, hydrogels, etc. Embodiments with compliant portions could be placed in a deflated state and then inflated to the appropriate thickness. Alternatively, bearing members may be filled with other flowable materials including beads or other particles made of metal, polymer, or foam material, optionally in a liquid medium, which conform to the adjacent bone or tissue surfaces. Thixotropic materials, such as hydrogels derived from hyaluronic acid, change their mechanical properties as shear stress is applied to them. An implant filled with such materials could be made to change the amount of displacement that it provides based on the shear stress that it sees from overlying target tissues at various points in the gait cycle. Implants may be coated with materials to reduce friction such as hydrophilic coatings or polytetrafluoroethylene (PTFE) coatings. Additionally or alternatively, the prosthesis may be adjustable to allow the dimensions such as thickness of the prosthesis to be adjusted during surgery or any time after surgery.

Rigid or substantially rigid prostheses according to embodiments of the invention described herein could be made of known bone-compatible implant materials such as titanium or stainless steel. Biocompatible polymers, ceramics, and other materials may also be used. The bearing surface of the prostheses should be designed to minimize negative effects of movement of the connective tissues across the implant surface, e.g. comprising a smooth, atraumatic, low-friction material, coating or surface treatment. Such prostheses could be implanted arthroscopically or using a mini-open or open surgical approach.

In various alternative embodiments, the displacement portion and the fixation portion of prostheses according to the invention may be of unibody construction, or may be formed of two or more parts depending on desired function. For example, the fixation portion may be stainless steel or titanium textured to enhance bony ingrowth and solid screw fixation, while the displacement portion could be made of a different material, for example, pyrolytic carbon to enhance the ability of overlying tissues to slide across the implant, or PTFE, silicone or other low-friction polymer with suitable wear characteristics to provide a softer bearing surface. In this regard, the displacement portion may comprise a separate bearing member with a bearing surface on which the target tissue bears. Alternatively the bearing surface may be formed as an integral part of the displacement portion. In further alternatives, the displacement portion could be comprised of a substrate of one material with an overlying layer forming the bearing member. The substrate could be either attached to or contiguous with the fixation portion. In other embodiments, the fixation portion of the implant may have a relief feature to minimize contact with the underlying bone, thereby minimizing disruption of the periosteal layer.

Generally, the bearing member and/or bearing surface in embodiments of the invention will be hard and smooth, made from materials such as polished pyrolytic carbon, steel, or titanium, or coated or covered with a lubricious material, such as PTFE. However, in embodiments where relative motion is provided for within the prosthesis itself, such as in exemplary embodiments described herein below, the bearing surface may be designed to encourage adhesion and ingrowth of the connective tissue onto this surface. For example, such a surface may be porous, roughened, or configured with openings into which bone or scar tissue may grow to enhance adhesion.

In some embodiments, the implant could be anchored to the underlying bone with suitable fasteners such as screws. Depending on the location and surgical need, unicortical screws, bicortical screws, cancellous screws, cannulated screws, polyaxial screws, screws that lock into the implant etc. may be used. In some embodiments, the screw holes may be locking threads or other locking features. In other embodiments, the screws holes may be oriented in different directions to improve the stability of the anchored implant. In alternate embodiments, different types of screws may be used in different regions of the implant. For example, cortical screws may be used in the region of the implant in contact with the femoral shaft while cancellous screws may be used in another part of the implant in contact with femoral condyle. Depending on patient anatomy and geometry of a specific implant, it may be desirable to provide supplemental fixation (such as cancellous bone screws) in the spanning section.

As discussed above, joint pain, joint stiffness or joint osteoarthritis may result from cranial tibial translation caused by cruciate ligament disease. By caudally displacing the caudal muscles or tendons like the semitendinosus, semimembranosus or biceps femoris muscle or tendon, the moment arm of the muscle or tendon as it crosses the joint may be increased, thereby stabilizing the joint during the gait cycle. By cranially displacing the cranial muscles or tendons like the quadriceps muscle or tendon, or patellar tendon, the moment arm of the muscle or tendon as it crosses the joint may be increased, thereby stabilizing the joint during the gait cycle. Other muscles and tendons around the knee that contribute to the cranio-caudal stability of the knee may also be displaced to achieve a similar therapeutic effect.

In one embodiment, displacement of the target tissue results in the decrease in the cranial tibial translation or thrust in the target stifle joint by at least about 0.5 mm, more preferably by at least about 1 mm, most preferably by at least about 1.5 mm. Reduction in cranial translation as defined here refers to decrease in translation, either maximum or average translation, either measured or calculated, during a normal gait cycle, running, jogging or any other physical activity which results in mechanical loading of articular cartilage in a stifle joint.

As discussed above, FIG. 9 shows one exemplary embodiment of the present invention for cranial displacement of the quadriceps muscle or tendon. Implant 100 is anchored to the medial side of the femur. Fixation portion 101 of the implant is used to anchor the implant, e.g. with screws 110, and displacement portion 103 displaces the quadriceps muscle or tendon cranially. Spanning section 102 would be configured to transition from fixation portion 101 mostly parallel to the medial side of the femur to displacement portion 103, which is disposed on a more cranial aspect of the femur so as to displace the quadriceps muscle or tendon cranially.

Figure 10:
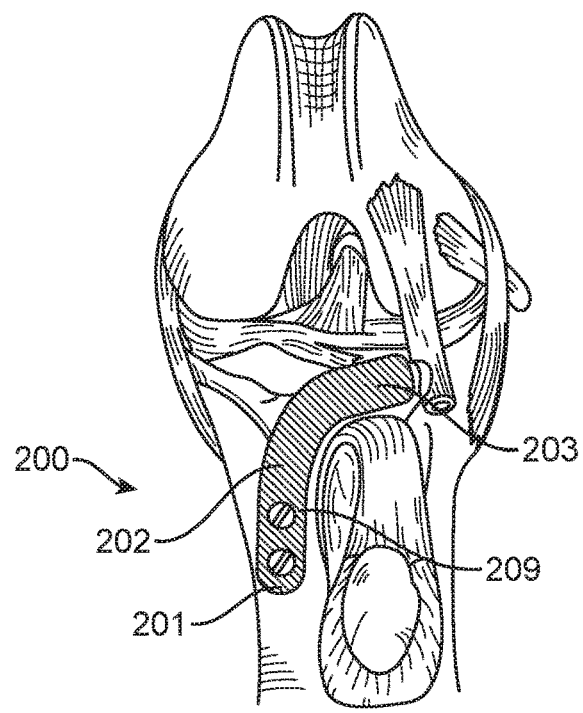
FIG. 10 is a cranial view of a left canine stifle joint illustrating positioning of another exemplary embodiment of the present invention for treating cruciate ligament disease.

FIG. 10 shows another exemplary embodiment of the present invention for cranial displacement of the patellar tendon. In this embodiment, implant 200 may be anchored to the medial side of the tibia. Fixation portion 201 of the implant is used to anchor the implant, e.g. with screws, and displacement portion 203 displaces the patellar tendon cranially. Advantageously, the fixation portion is separated from the displacement portion by spanning section 202 so that the fixation portion may be shaped and dimensioned to optimize anchoring, holes 209 for screws may be more numerous and separated further apart, and the location on the bone for anchoring may be more easily accessed and visualized by the surgeon. Displacement portion 203 preferably has a convex curvature on its outer tissue-engaging surface (bearing surface), preferably being curved at least around an axis generally parallel to the tibial shaft, usually being curved also around an axis perpendicular to the tibial shaft, and more preferably being spherical or partially spherical. Displacement portion 203 is disposed over a more cranial aspect of the tibia so as to be located under the patellar tendon between the tendon insertion point and the dorsal end of the tibia.

In embodiments of the present invention, implants may be configured such that the displacement portion of the implant is separated from the fixation portion of the implant. With the displacement portion positioned under the target tissue (e.g. patellar tendon), the fixation portion of the implant may be configured to be affixed to the bone at a location which can securely fix the implant in place, is accessible to the surgeon, is not covered by the target tissue, and is separated from tendon insertion points and other anatomical features. The implant may have a spanning section configured and dimensioned to bridge the distance between the fixation portion and the displacement portion. The implants may be configured to move the tendon anteriorly or medially or anterior-medially or laterally or antero-laterally. This may be accomplished by making one side (lateral or medial) of the displacement surface higher than the other, and/or by forming a track with ridges on one or both sides of the bearing surface to urge the tendon in a lateral or medial direction.

Figure 11:
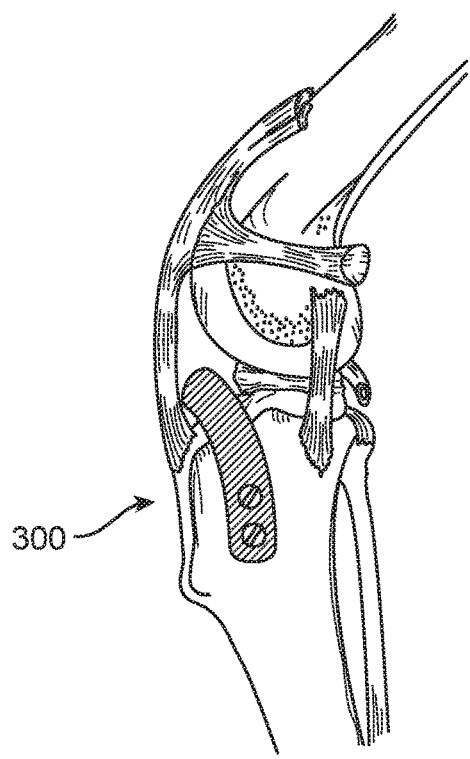
FIG. 11 is a medial view of a right canine stifle joint illustrating positioning of a further exemplary embodiment of the present invention for treating cruciate ligament disease.

FIG. 11 shows an exemplary embodiment of the present invention for cranial displacement of the patellar tendon. Implant 300 is anchored to the medial side of the tibia.

Figure 12:
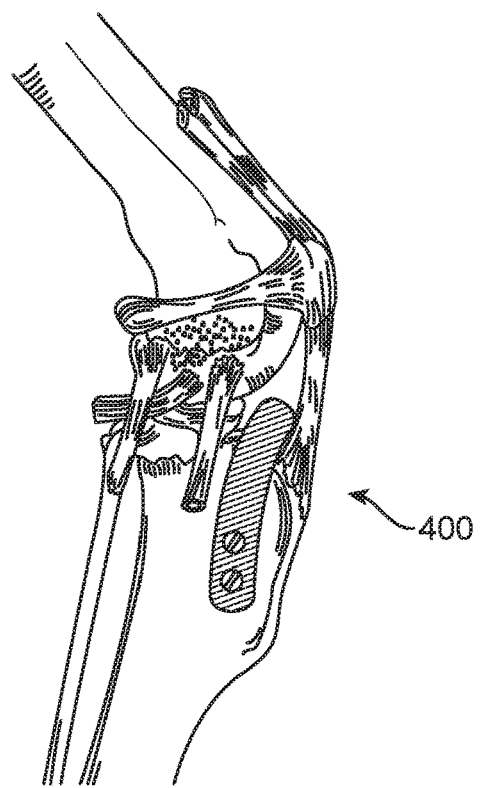
FIG. 12 is a lateral view of a right canine stifle joint illustrating positioning of yet another exemplary embodiment of the present invention for treating cruciate ligament disease.

FIG. 12 shows an exemplary embodiment of the present invention for cranial displacement of the patellar tendon. Implant 400 is anchored to the lateral side of the tibia.

Figure 13:
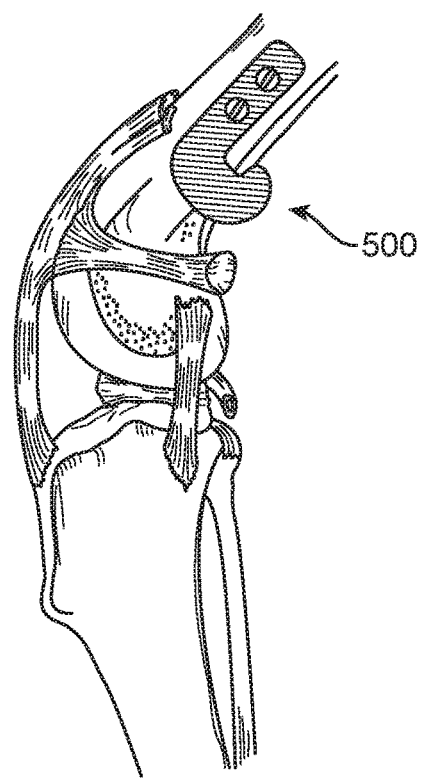
FIG. 13 is a medial view of a right canine stifle joint illustrating positioning of another exemplary embodiment of the present invention for treating cruciate ligament disease.

FIG. 13 shows an exemplary embodiment of the present invention for caudal displacement of the hamstring muscles. Implant 500 is anchored to the medial side of the femur. Implant 500 has a displacement portion configured to be located along a caudal aspect of the femur under the hamstring muscle so as to displace the hamstring caudally, that is, away from the femoral shaft.

Figure 14:
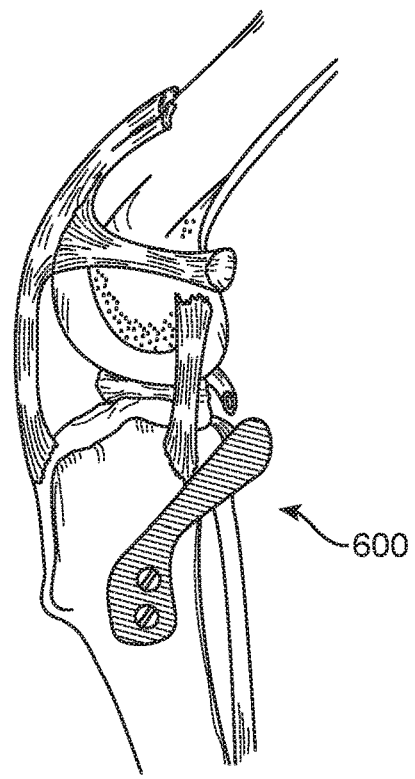
FIG. 14 is a medial view of a right canine stifle joint illustrating positioning of another exemplary embodiment (#600) of the present invention for treating cruciate ligament disease.

FIG. 14 shows an exemplary embodiment of the present invention for caudal displacement of the hamstring muscles. Implant 600 is anchored to the medial side of the tibia.

Figure 15:
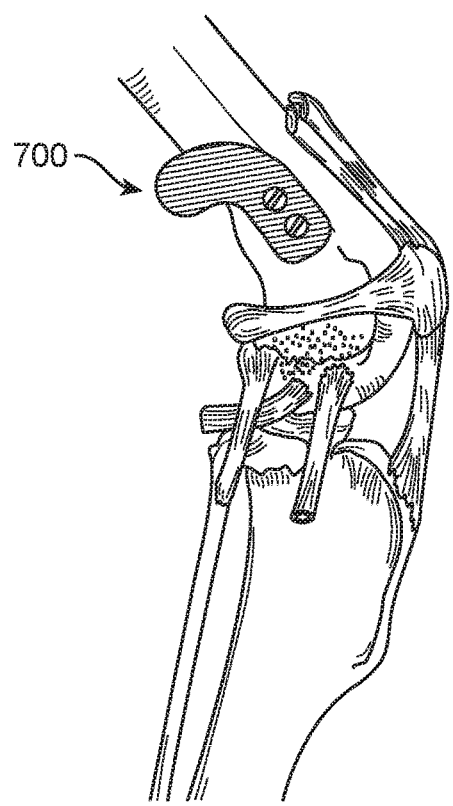
FIG. 15 is a lateral view of a right canine stifle joint illustrating positioning of another exemplary embodiment of the present invention for treating cruciate ligament disease.

FIG. 15 shows an exemplary embodiment of the present invention for caudal displacement of the hamstring muscles. Implant 700 is anchored to the lateral side of the femur.

Figure 16:
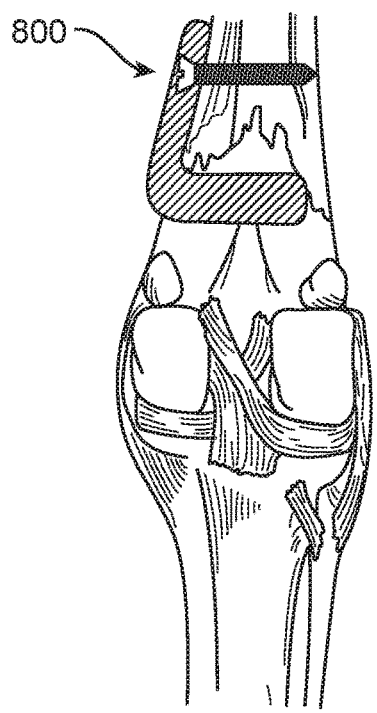
FIG. 16 is a caudal view of a right canine stifle joint illustrating positioning of another exemplary embodiment of the present invention for treating cruciate ligament disease.

FIG. 16 shows an exemplary embodiment of the present invention for caudal displacement of the hamstring muscles. Implant 800 is anchored to the medial side of the femur.

Figure 17:
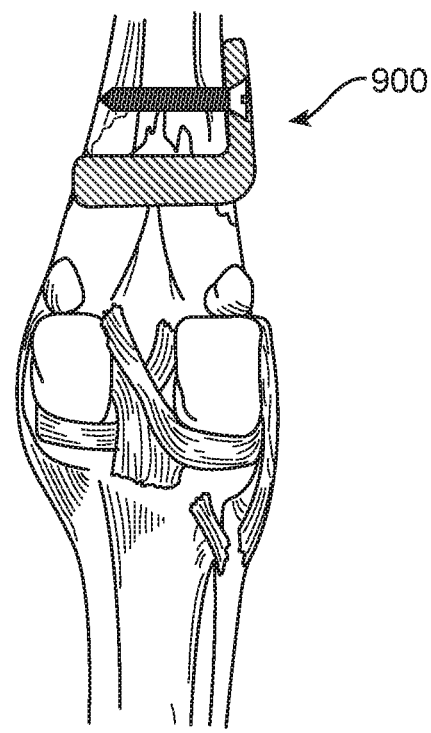
FIG. 17 is a caudal view of a right canine stifle joint illustrating positioning of another exemplary embodiment of the present invention for treating cruciate ligament disease.

FIG. 17 shows an exemplary embodiment of the present invention for caudal displacement of the hamstring muscles. Implant 900 is anchored to the lateral side of the femur.

Figure 18:
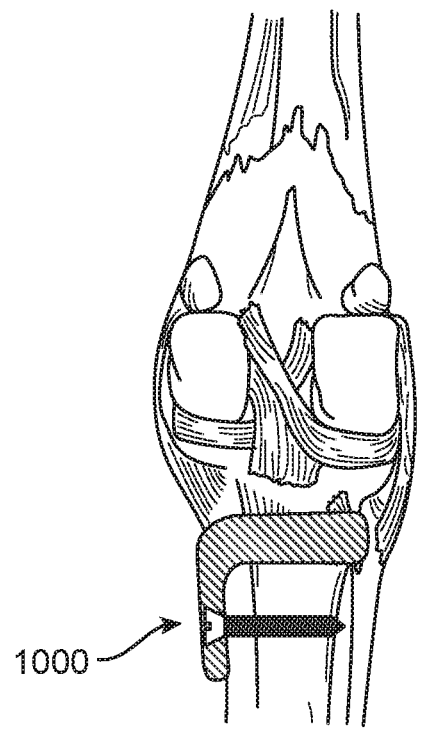
FIG. 18 is a caudal view of a right canine stifle joint illustrating positioning of another exemplary embodiment of the present invention for treating cruciate ligament disease.

FIG. 18 shows an exemplary embodiment of the present invention for caudal displacement of the hamstring muscles. Implant 1000 is anchored to the medial side of the tibia.

Figure 19:
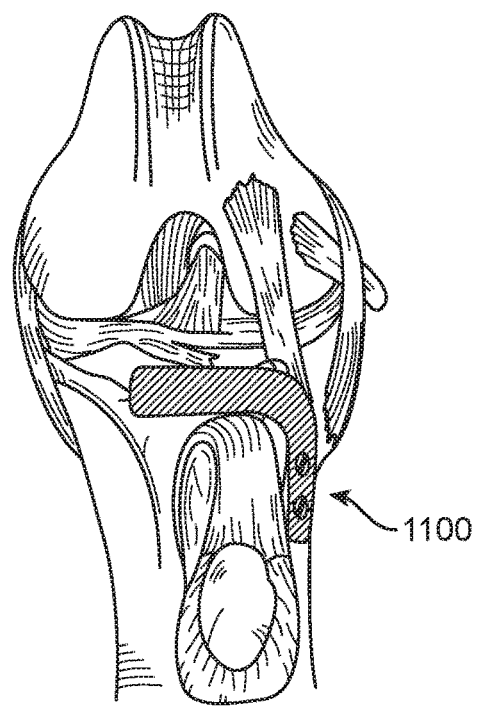
FIG. 19 is a cranial view of a left canine stifle joint illustrating positioning of another exemplary embodiment of the present invention for treating cruciate ligament disease.

FIG. 19 shows an exemplary embodiment of the present invention for cranial displacement of the patellar tendon. Implant 1100 is anchored to the lateral side of the tibia.

Figure 20:
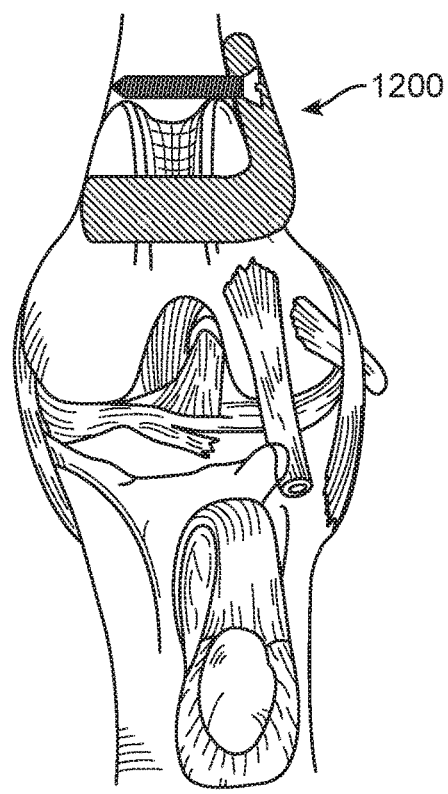
FIG. 20 is a cranial view of a left canine stifle joint illustrating positioning of another exemplary embodiment of the present invention for treating cruciate ligament disease.

FIG. 20 shows an exemplary embodiment of the present invention for cranial displacement of the quadriceps muscle or tendon. Implant 1200 is anchored to the lateral side of the femur.

As with other embodiments described herein, the displacement of the target tissue can be altered by changing the length, curvature and angle of the spanning section and/or dimensions of the displacement and fixation portions as appropriate for specific canine anatomy.

The spanning sections may also comprise adjustable mechanisms (e.g. a pin or hinge) to movably or pivotably alter the orientation or angle between the two parts to achieve the appropriate level of tissue displacement.

In some embodiments of the present invention, the displacement of the connective tissue could be adjusted by adjusting the device pre-operatively, intra-operatively or post-operatively. Devices may include mechanisms that are remotely controlled and/or enable wireless communication to alter the displacement after implantation. Alternatively, the displacement may be adjusted by applying an energy fields (e.g.; magnetic field, electric field, thermal field etc.) transdermally from an external location.

In various adjustable embodiments described above, the adjustment mechanisms themselves may be radiopaque and/or otherwise discernable from the rest of the implant under x-ray in order to enable post-surgical percutaneous adjustment of the device. Alternatively, target features can be built into the device to locate the adjustment points without having the screws or adjustment means themselves radiopaque, such as radiopaque rings or markers built into the nearing surface of the device itself.

The implants described above may be implanted in areas adjacent to the joint such that the soft tissue is displaced in a region it crosses the joint. Alternatively, the device could be implanted away from the joint and displace the target soft tissue in a region that it is not crossing the joint.

In other alternative embodiments, displacement portions of previously described static implants may be provided with a roller or other dynamic feature to further reduce wear or trauma to the displaced tissue. In some embodiments, the inferior surface of the displacement region is elevated off the underlying tissue. The underlying tissue could be bone or soft tissue like tendon, muscle, ligament, bursa, capsule etc. Elevating the inferior surface off the underlying tissue could be beneficial by minimizing damage to soft tissue, reducing any potential restriction to joint motion due to compression of soft tissue etc.

In some embodiments, the displacement region will have a continuous bearing surface which is in contact with the target connective tissue (muscle, tendon, ligament etc.) and is devoid of any discontinuities. Discontinuities would include fixation channels for long-term fixation like screw holes, holes for sutures etc. as well as fixation channels for temporary fixation like holes for Kirschner-wires (K-wires). The lack of discontinuities in the bearing surface would minimize the potential for wear or irritation of the target connective tissue. The bearing surface of the displacement section may be polished, coated or modified in other ways to minimize wear of the bearing surface and/or wear of the target connective tissue.

In some embodiments, the bearing surface of the displacement region which is in contact with the target connective tissue (muscle, tendon, ligament etc.) may have features that enable adhesion or attachment of the target connective tissue to the bearing surface. Attachment of the target connective tissue on the implant surface may minimize motion of the tissue across the implant surface during joint motion. These features would include channels for formation of fibrous tissue from the target connective tissue anchoring the connective tissue to the displacement surface of the implant.

In some embodiments, the bearing surface of the displacement region may have surface features that enable adhesion or attachment of the target connective tissue to the bearing surface. These features would include projections, microprojections, bumps, ridges, pin-like projections, granular surface etc.

In some embodiments, the inferior surface of the displacement region may be in contact with the underlying tissue. In other embodiments, part of the inferior surface of the displacement section may be in contact with the underlying tissue.

In some embodiments, the inferior region may have features like channels for fibrous or bony tissue ingrowth to enable adhesion or attachment of the underlying tissue to the bearing surface. In other embodiments, the inferior region may have features like projections, microprojections, bumps, ridges, pin-like projections, granular surface etc. Attachment of any soft connective tissue underneath the inferior surface of the displacement region may minimize motion of the tissue under the implant during joint motion. In other embodiments, the inferior surface may have pins for anchoring the implanting into underlying bone.

In some embodiments, the device may be a two-part device with the first part (base unit) comprising the fixation section, the spanning section and the displacement section, and the second part (bearing unit) configured to attach to the displacement section of the base unit. In other embodiments the bearing unit may be configured to attach to the spanning section and to cover the displacement section of the base unit. The bearing unit may be configured to minimize tissue wear or to enable tissue adhesion or attachment. In one embodiment, the displacement section and the bearing unit would have features to attach the two units.

In some embodiments, the displacement region may have channels to assist in positioning, placement or temporarily anchoring of the implant intra-operatively.

As will be evident to one skilled in the art, the dimensions of the exemplary embodiments above can be altered to address differences in joint size, condyle size, level of the tissue displacement etc. as well as to enable positioning and securing the implant at the surgical site while minimizing trauma to the surrounding bone, tendons, muscles, ligaments and other anatomical structures.

While the invention has been illustrated by examples in various contexts, the devices of the present invention may be used to displace any of the muscles and connective tissues around the stifle joint to achieve a therapeutic effect. For example, the muscle displaced could be the popliteus muscle, gastrocnemius muscle, vastus lateralis muscle, vastus medialis muscle and the semimembranous muscle. Alternatively, the tendon associated with any of the muscles could be displaced.

While the invention has been illustrated by examples in various contexts of treating canine cruciate ligament disease, it will be understood that the invention may also have application to treatment of other animals like cats, horses etc.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

The invention claimed is:

1. A device for treating canine cruciate ligament disease in a canine stifle joint, comprising an implant configured and dimensioned to be secured to a canine tibia and to extend under the canine patellar tendon, and to displace the canine patellar tendon sufficiently to produce a therapeutic effect selected from reducing pain, reducing cranial tibial thrust, or increasing stability of the canine stifle joint, wherein said implant comprises:
a fixation portion configured to be secured to one of the lateral side or the medial side of the canine tibia; and
a displacement portion extending centrally from a cranial end of the fixation portion and configured and dimensioned to lie over a more cranial aspect of the tibia relative to the fixation portion positioned under the patellar tendon, and further configured to atraumatically contact and displace the patellar tendon sufficiently to produce at least one said therapeutic effect.

2. The device of claim 1, wherein the displacement portion includes a bearing surface comprising a smooth surface free of discontinuities to atraumatically engage and displace the target tissue.

3. The device of claim 2, further comprising a spanning section disposed between the fixation portion and displacement portion.

4. The device of claim 3, wherein the spanning section and displacement portion are configured and dimensioned to position the bearing surface so as to displace the target tissue greater than about 2 mm up to about 25 mm beyond the natural anatomical track of the target tissue.

5. The device of claim 4, wherein said displacement is in the range of about 4-15 mm.

6. A device for treating canine cruciate ligament disease in a canine stifle joint by displacing the canine patellar tendon, the device comprising:
a fixation portion configured to be mounted to a canine tibia at a fixation site proximate the upper tibial extremity and medially or laterally of the tibial tuberosity;
a spanning section configured and dimensioned to extend cranially and laterally or medially from the fixation portion in a direction towards the tibial mid-line; and
a displacement portion having an overall curvature around an axis generally parallel to the tibial shaft when the fixation portion is mounted at the fixation site and configured and dimensioned to (i) extend from the spanning section further laterally or medially under patellar tendon and in engagement therewith, and (ii) displace the patellar tendon cranially, anteriorly, medially, anterior-medially or laterally or antero-laterally sufficiently to alter the location, angle or magnitude of forces exerted thereby on the patella so as to achieve a therapeutic effect in patellofemoral compartment of the knee.

7. The device of claim 6, wherein the therapeutic effect comprises a reduction of loading on an articular surface associated with the canine patella.

8. The device of claim 6, wherein the displacement portion includes a bearing surface configured to atraumatically engage the canine patellar tendon, the bearing surface being free of holes or other fixation means.

9. The device of claim 6, wherein said displacement portion and spanning section are configured and dimensioned in combination to displace the canine patellar tendon from a pre-treatment anatomical path by displacement distance of more than about 2 mm and less than about 25 mm when the fixation portion is mounted to the tibia.

10. The device of claim 9, wherein said displacement is between about 4 mm to about 15 mm.

11. The device of claim 6, wherein:
the fixation portion is disposed at an angle with the spanning section such that with the prosthesis implanted and the displacement portion engaging the canine patellar tendon, the fixation portion is substantially aligned with the tibial shaft; the spanning section is configured and dimensioned to avoid contact with the medial edge of the canine patellar tendon; and
the displacement portion is further configured and dimensioned to lie substantially parallel to the axis of the tibial plateau when the fixation portion is secured medially of the tibial tuberosity with the fixation portion substantially aligned with the tibial shaft.

12. A device for treating canine cruciate ligament disease in a canine stifle joint by displacing the canine patellar tendon, the device comprising:
a fixation portion configured to be mounted to a canine tibia at a fixation site proximate the upper tibial extremity and medially or laterally of the tibial tuberosity; and
a displacement portion defining a bearing surface and having an overall curvature around an axis generally parallel to the tibial shaft when the fixation portion is mounted at the fixation site, wherein:
the displacement portion is configured and dimensioned to extend laterally or medially under patellar tendon and in engagement therewith;
the bearing surface is free of holes or other fixation means configured to atraumatically engage the canine patellar tendon; and
the device is configured and dimensioned to position the bearing surface, when the fixation portion is mounted at the fixation site on the tibia, to displace the patellar tendon from a pre-treatment anatomical path by displacement distance of more than about 2 mm and less than about 25 mm when the fixation portion is mounted to the tibia so as to reduce loading on an articular surface in the patellofemoral compartment of the knee.

13. The device of claim 12, further comprising a spanning section configured and dimensioned to extend cranially and laterally or medially from the fixation portion in a direction towards the tibial mid-line to join with the displacement portion to space the displacement portion from the fixation portion thereby.

* * * * *